(12) United States Patent  
Berthelette et al.

(10) Patent No.: US 7,199,154 B2
(45) Date of Patent: Apr. 3, 2007

(54) NITRIC OXIDE RELEASING PRODRUGS OF DIARYL-2-(5H)-FURANONES AS CYCLOOXYGENASE-2 INHIBITORS

(75) Inventors: Carl Berthelette, Ste-Dorothee Laval (CA); Nicholas Lachance, Montreal (CA); Lianhai Li, Montreal (CA); Claudio Sturino, L'ile-Bizard (CA); Zhaoyin Wang, Kirkland (CA); Robert N. Young, Senneville (CA); Claude Dufresne, Dollard Des Ormeaux (CA)

(73) Assignee: Merck Frosst Company, Kirkland, Quebec (CA)

( * ) Notice: Subject to any disclaimer, the term of this patent is extended or adjusted under 35 U.S.C. 154(b) by 159 days.

(21) Appl. No.: 10/521,075

(22) PCT Filed: Jul. 24, 2003

(86) PCT No.: PCT/CA03/01115

§ 371 (c)(1),
(2), (4) Date: Jan. 12, 2005

(87) PCT Pub. No.: WO2004/011421

PCT Pub. Date: Feb. 5, 2004

(65) Prior Publication Data

US 2005/0261245 A1    Nov. 24, 2005

Related U.S. Application Data

(60) Provisional application No. 60/435,341, filed on Dec. 20, 2002, provisional application No. 60/398,683, filed on Jul. 26, 2002.

(51) Int. Cl.
*C07C 317/46* (2006.01)
*A61K 31/216* (2006.01)
*A61P 29/00* (2006.01)

(52) U.S. Cl. .................... 514/509; 558/482
(58) Field of Classification Search ............. 558/482; 514/509
See application file for complete search history.

(56) References Cited

U.S. PATENT DOCUMENTS

| 5,733,909 | A | 3/1998 | Black et al. |
| 5,849,943 | A | 12/1998 | Atkinson et al. |
| 6,649,629 | B2 | 11/2003 | Bandarage et al. |
| 6,706,724 | B2 | 3/2004 | Khanapure et al. |
| 2001/0041726 | A1 | 11/2001 | Bandarage et al. |
| 2003/0220228 | A1 | 11/2003 | Bandarage et al. |
| 2004/0053985 | A1 | 3/2004 | Bandarage et al. |
| 2004/0072883 | A1 | 4/2004 | Garvey et al. |
| 2004/0116431 | A1 | 6/2004 | Khanapure et al. |
| 2004/0176331 | A1* | 9/2004 | Berthelette et al. ......... 514/114 |
| 2005/0192346 | A1* | 9/2005 | Shi et al. .................... 514/509 |

FOREIGN PATENT DOCUMENTS

| EP | 1 336 602 A1 | 8/2003 |
| WO | WO 94/12463 | 6/1994 |
| WO | WO 95/30641 | 11/1995 |
| WO | WO 96/13483 | 4/1997 |
| WO | WO 97/16405 | 5/1997 |
| WO | WO 97/28120 | 8/1997 |
| WO | WO 01/45703 A1 | 6/2001 |
| WO | WO 03/094924 A1 | 11/2003 |
| WO | WO 03/103602 A2 | 12/2003 |
| WO | WO 2004/000300 A1 | 12/2003 |
| WO | WO 2004/000781 A2 | 12/2003 |

OTHER PUBLICATIONS

Blaine et al., J. Shoulder Elbow Surg, 14(1S), 84S-89S, 2005.*
Kim et al., Clinical Therapeutics, 25(6), 1593-1617, 2003.*
Nogawa et al., International Congress Series, 1215, 363-372, 2003.*
Takasaki et al., Neuropharmacology, 49, 283-292, 2005.*
Golub et al., Science, 286, 531-537, Oct. 15, 1999.*

* cited by examiner

*Primary Examiner*—Fiona T. Powers
(74) *Attorney, Agent, or Firm*—Raynard Yuro; David L. Rose

(57) ABSTRACT

The invention encompasses novel compounds of Formula I, which are nitric oxide-releasing prodrugs of diaryl-2-(5H) furanones useful in the treatment of cyclooxygenase-2 mediated diseases. The invention also encompasses certain pharmaceutical compositions and methods for treatment of cyclooxygenase-2 mediated diseases comprising the use of compounds of Formula I. The above compounds may be used as a combination therapy with low-dose aspirin to treat chronic cyclooxygenase-2 mediated diseases or conditions while simultaneously reducing the risk of thrombotic cardiovascular events

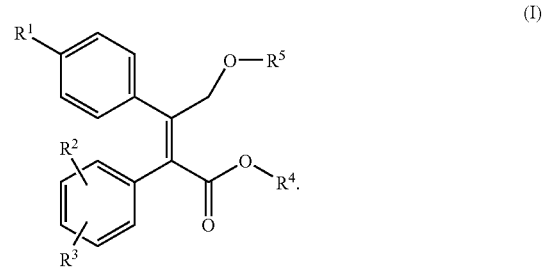

(I)

18 Claims, No Drawings

NITRIC OXIDE RELEASING PRODRUGS OF DIARYL-2-(5H)-FURANONES AS CYCLOOXYGENASE-2 INHIBITORS

CROSS REFERENCE TO RELATED APPLICATIONS

This application is a U.S. National Phase application under 35 U.S.C. § 371 of PCT Application No. PCT/CA03/01115, filed Jul. 24, 2003, which claims priority under 35 U.S.C. 119 to U.S. No. 60/435,341, filed Dec. 20, 2002 and 60/398,683, filed Jul. 26, 2002.

BACKGROUND OF THE INVENTION

Selective inhibitors of cyclooxygenase-2 are a sub-class of the class of drugs known as non-steroidal antiinflammatory drugs (NSAIDs). The NSADs are active in reducing the prostaglandin-induced pain and swelling associated with the inflammation process but are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandin by inhibiting enzymes in the human arachidonic acid/prostaglandin pathway including the enzyme cyclooxygenase (COX). The discovery that there are two isoforms of the COX enzyme, the first, COX-1, being involved with physiological functions and the second, COX-2, being induced in inflamed tissue, has given rise to a new approach. While conventional NSAIDs block both forms of the enzyme, the identification of the inducible COX-2 enzyme associated with inflammation has provided a viable target of inhibition which more effectively reduces inflammation and produces fewer and less drastic side effects. Many compounds which have activity as COX-2 inhibitors have been identified, including rofecoxib (VIOXX®), etoricoxib (ARCOXIA™), celecoxib (CELEBREX®) and valdecoxib (BEXTRA™), and much research continues in this area.

Many patients with a chronic cyclooxygenase-2 mediated disease or condition are elderly and thus are at increased risk for thrombotic cardiovascular events, such as stroke, myocardial ischemia, myocardial infarction, angina pectoris, transient ischemic attack (TIA; amaurosis fugax), reversible ischemic neurologic deficits, and any similar thrombotic event in any vascular bed (splanchnic, renal, aortic, peripheral, etc.). Moreover, there is evidence that patients with chronic inflammatory conditions, such as rheumatoid arthritis and systemic lupus erythematosis are at increased risk for thrombotic cardiovascular events. Thus, it is desirable that such patients receive appropriate therapy to reduce their risk of such events.

NO-releasing forms of non-steroidal anti-inflammatory drugs are known in the art and are reported to have improved gastrointestinal and cardiovascular safety profiles over their conventional NSAID counterparts. Furthermore, NO-releasing forms of selective cyclooxygenase-2 selective inhibitors are disclosed in WO 01/45703, published on Jun. 28, 2001.

The present invention provides for novel nitrosated or nitrosylated prodrugs for cyxlooxygenase-2 selective inhibitors that are useful for treating cyclooxygenase-2 mediated diseases or conditions which can be administered alone or in combination with low-dose aspirin. Thus, the invention provides for a clearly superior profile than that hitherto obtainable in that it provides efficacy in treating chronic cyclooxygenase-2 mediated diseases or conditions, effectively reducing the risk of thrombotic cardiovascular events and possibly renal side effects and at the same time reduces the risk of GI ulceration or bleeding.

SUMMARY OF THE INVENTION

The invention encompasses novel compounds of Formula I, which are nitric oxide-releasing prodrugs of diaryl-2-(5H) furanones useful in the treatment of cyclooxygenase-2 mediated diseases.

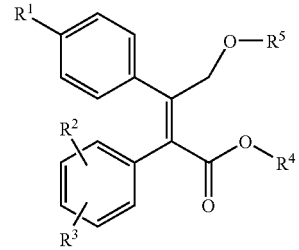

The invention also encompasses certain pharmaceutical compositions and methods for treatment of cyclooxygenase-2 mediated diseases comprising the use of compounds of Formula I. The above compounds may be used as a combination therapy with low-dose aspirin to treat chronic cyclooxygenase-2 mediated diseases or conditions while simultaneously reducing the risk of thrombotic cardiovascular events.

DETAILED DESCRIPTION OF THE INVENTION

The invention encompasses the novel compound of Formula I as a prodrug which converts in vivo to diaryl-2-(5H)-furanones useful in the treatment of cyclooxygenase-2 mediated diseases

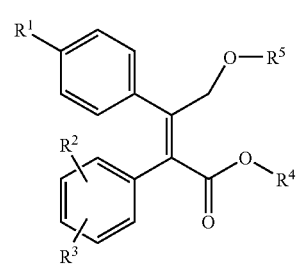

I or a pharmaceutically acceptable salt thereof, wherein $R^1$ is selected from the group consisting of:
(a) $S(O)_2CH_3$,
(b) $S(O)_2NH_2$,
(c) $S(O)_2NHC(O)CF_3$,
(d) $S(O)(NH)CH_3$,
(e) $S(O)(NH)NH_2$,
(f) $S(O)(NH)NHC(O)CF_3$,
(g) $P(O)(CH_3)OH$, and
(h) $P(O)(CH_3)NH_2$;

$R^2$ and $R^3$ each are independently selected from the group consisting of:
(a) hydrogen,
(b) halo,
(c) $C_{1-6}$alkoxy,
(d) $C_{1-6}$alkylthio,
(e) CN,
(f) $CF_3$,
(g) $C_{1-6}$alkyl, and
(h) $N_3$;

$R^4$ is selected from the group consisting of
(a) hydrogen,
(b) $C_{1-6}$alkyl, optionally substituted with 1–3 substituents independently selected from the group consisting of:
  (i) halo,
  (ii) phenyl, naphthyl or $HET^1$, each of said phenyl, naphthyl or $HET^1$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$,
  (iii) $N(R^i)R^{ii}$, wherein $R^i$ and $R^{ii}$ are each independently selected from the group consisting of hydrogen and $C_{1-4}$alkyl,
  (iv) —$CO_2R^{iii}$, wherein $R^{iii}$ is hydrogen or $C_{1-4}$alkyl,
(c) phenyl, naphthyl or $HET^2$, each optionally substituted with 1-3 substituents independently selected from the group consisting of: halo, $C_{1-6}$alkyl, $C_{1-6}$alkoxy, $C_{1-6}$alkylthio, OH, CN, $CF_3$, and $CO_2R^6$;

$R^5$ is selected from the group consisting of:

(a) —$NO_s$, (b) —$C(O)$—E—$C_{1-10}$alkyl—W—$NO_s$,

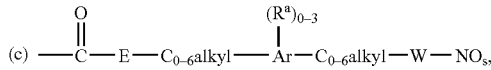

wherein:
each s is independently 1 or 2,
E is a bond, oxygen, sulfur or —C(O)—O—,
each W is independently selected from the group consisting of:

(1) oxygen, (2) sulfur, (3) 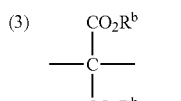

(4) 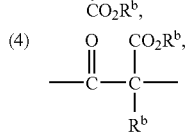

Ar is selected from the group consisting of: phenyl, naphthyl and $HET^3$,
each $R^a$ is independently selected from the group consisting of:
(1) halo,
(2) $C_{1-6}$alkyl,
(3) $C_{1-6}$alkoxy,
(4) $C_{1-6}$alkylthio, (5) OH,
(6) CN,
(7) $CF_3$,
(8) $CO_2R^7$, and
(9) $C_{0-6}$alkyl-W—$NO_S$;

each Rb is independently selected from the group consisting of:
(1) $C_{1-6}$alkyl, optionally substituted with 1–3 halo groups or optionally substituted with phenyl, naphthyl or $HET^4$, each of said phenyl, naphthyl or $HET^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and
(2) phenyl, naphthyl or $HET^5$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;

$R^6$, $R^7$ and $R^8$ are each independently selected from the group consisting of
(a) hydrogen,
(b) $C_{1-6}$alkyl; and $HET^1$, $HET^2$, $HET^3$, $HET^4$ and $HET^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrinidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

The invention also encompasses a compound of Formula I

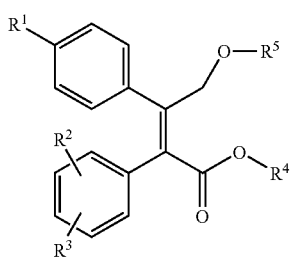

or a pharmaceutically acceptable salt thereof wherein
$R^1$ is selected from the group consisting of.
(a) $S(O)_2CH_3$,
(b) $S(O)_2NH_2$,
(c) $S(O)_2NHC(O)CF_3$, (d) S(O)(NH)CH$_3$,
(e) S(O)(NH)NH$_2$,
(f) S(O)(NH)NHC(O)CF$_3$,
(g) P(O)(CH$_3$)OH, and
(h) P(O)(CH$_3$)NH$_2$;

R$^2$ and R$^3$ each are independently selected from the group consisting of:
(a) hydrogen,
(b) halo,
(c) C$_{1-6}$alkoxy,
(d) C$_{1-6}$alkylthio,
(e) CN,
(f) CF$_3$,
(g) C$_{1-6}$alkyl, and
(h) N$_3$;

R$^4$ is selected from the group consisting of
(a) hydrogen,
(b) C$_{1-6}$alkyl, optionally substituted with 1–3 halo groups or optionally substituted with phenyl, naphthyl or HET$^1$, each of said phenyl, naphthyl or HET$^1$ being optionally substituted with 1–3 substituents independently selected from the group consisting of: halo, C$_{1-6}$alkyl, C$_{1-6}$alkoxy, C$_{1-6}$alkylthio, OH, CN, CF$_3$, and CO$_2$R$^6$;
(c) phenyl, naphthyl or HET$^2$, each optionally substituted with 1–3 substituents independently selected from the group consisting of: halo, C$_{1-6}$alkyl, C$_{1-6}$alkoxy, C$_{1-6}$alkylthio, OH, CN, CF$_3$, and CO$_2$R$^6$;

R$^5$ is selected from the group consisting of:

(a) —NO$_s$, (b) —C(O)—E—C$_{1-10}$alkyl—W—NO$_s$, (c) 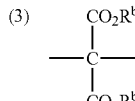

wherein:
each s is independently 1 or 2,
E is a bond, oxygen, sulfur or —C(O)—O—,
each W is independently selected from the group consisting of:

(1) oxygen,
(2) sulfur, (3) 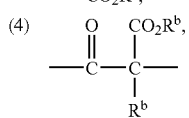

(4)

Ar is selected from the group consisting of: phenyl, naphthyl and HET$^3$, each R$^a$ is independently selected from the group consisting of:
(1) halo,
(2) C$_{1-6}$alkyl,
(3) C$_{1-6}$alkoxy,
(4) C$_{1-6}$alkylthio,
(5) OH,
(6) CN,
(7) CF$_3$,
(8) CO$_2$R$^7$, and
(9) C$_{0-6}$alkyl-W—NO$_s$;

each Rb is independently selected from the group consisting of:
(1) C$_{1-6}$alkyl, optionally substituted with 1–3 halo groups or optionally substituted with phenyl, naphthyl or HET$^4$, each of said phenyl, naphthyl or HET$^4$ being optionally substituted with 1–3 substituents independently selected from the group consisting of: halo, C$_{1-6}$alkyl, C$_{1-6}$alkoxy, C$_{1-6}$alkylthio, OH, CN, CF$_3$, and CO$_2$R$^8$; and
(2) phenyl, naphthyl or HET$^5$, each optionally substituted with 1–3 substituents independently selected from the group consisting of: halo, C$_{1-6}$alkyl, C$_{1-6}$alkoxy, C$_{1-6}$alkylthio, OH, CN, CF$_3$, and CO$_2$R$^8$;

R$^6$, R$^7$ and R$^8$ are each independently selected from the group consisting of
(a) hydrogen,
(b) C$_{1-6}$alkyl; and HET$^1$, HET$^2$, HET$^3$, HET$^4$ and HET$^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

The present compounds are nitric oxide releasing prodrugs which liberate nitric oxide and diaryl-2-(5H)-furanones useful as cyclooxygenase-2 selective inhibitors, such as rofecoxib, in vivo and can be administered alone or in combination with low dose aspirin. Thus, the invention provides for a clearly superior profile than that hitherto obtainable in that it provides efficacy in treating chronic cyclooxygenase-2 mediated diseases or conditions, effectively reducing the risk of thrombotic cardiovascular events and renal side effects and at the same time reduces the risk of GI ulceration or bleeding.

An embodiment of the invention encompasses a compound of Formula I wherein:
R$^1$ is S(O)$_2$CH$_3$, and
R$^2$ and R$^3$ are both hydrogen.

Within this embodiment of the invention is encompassed a compound of Formula I wherein:
R$^4$ is C$_{1-6}$alkyl, optionally substituted with 1–3 halo groups or optionally substituted with phenyl, naphthyl or HET$^1$, each of said phenyl, naphthyl or HET$^1$ being optionally substituted with 1–3 substituents independently selected from the group consisting of halo, $C_{1-6}$alkyl, $C_{1-6}$alkoxy, $C_{1-6}$alkylthio, OH, CN, $CF_3$, and $CO_2R^6$;

$R^6$ is selected from the group consisting of
(a) hydrogen,
(b) $C_{1-6}$alkyl; and $HET^1$ is selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl. Further within this embodiment of the invention is encompassed a compound of Formula I wherein $R^4$ is methyl, ethyl, propyl or isopropyl.

Another embodiment of the invention encompasses a compound of Formula I wherein:

$R^1$ is $S(O)_2CH_3$;

$R^2$ and $R^3$ are both hydrogen;

$R^4$ is phenyl, naphthyl or $HET^2$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;

$R^6$ is selected from the group consisting of
(a) hydrogen,
(b) $C_{1-6}$alkyl; and $HET^2$ is selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

Another embodiment of the invention encompasses a compound of Formula I wherein:

$R^1$ is $S(O)_2CH_3$;

$R^2$ and $R^3$ are both hydrogen;

$R^5$ is $-NO_S$; and s is 1 or 2.

Another embodiment of the invention encompasses a compound of Formula I wherein:

$R^1$ is $S(O)_2CH_3$;

$R^2$ and $R^3$ are both hydrogen;

$R^5$ is $-C(O)-E-C_{1-10}$alkyl-W$-NO_S$, wherein:

s is 1 or 2,

E is a bond, oxygen, sulfur or $-(O)-O-$,

W is selected from the group consisting of:

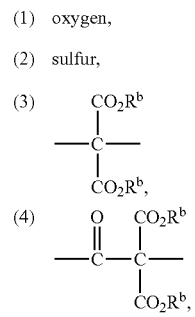

each $R^b$ is independently selected from the group consisting of:

(1) $C_{1-6}$alkyl, optionally substituted with 1–3 halo groups or optionally substituted with phenyl, naphthyl or $HET^4$, each of said phenyl, naphthyl or $HET^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and (2) phenyl, naphthyl or $HET^5$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;

$R^8$ is selected from the group consisting of
(a) hydrogen and
(b) $C_{1-6}$alkyl; and $HET^4$ and $HET^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl. Further within this embodiment, E is a bond or oxygen; s is 2; W is oxygen; and $R^4$ is hydrogen, methyl, ethyl, propyl or isopropyl.

Another embodiment of the invention encompasses a compound of Formula I wherein:
$R^1$ is $S(O)_2CH_3$;
$R^2$ and $R^3$ are both hydrogen;
$R^5$ is

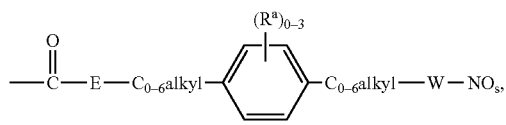

wherein:
each s independently 1 or 2,
E is a bond, oxygen, sulfur or —C(O)—O—,
each W is independently selected from the group consisting of:

(1) oxygen, (2) sulfur, (3) 
```
    CO₂R^b
    |
—C—
    |
    CO₂R^b,
```

(4)
```
    O   CO₂R^b
    ||  |
—C—C—
        |
        CO₂R^b,
``` each $R^a$ is independently selected from the group consisting of:
(1) halo,
(2) $C_{1-6}$alkyl,
(3) $C_{1-6}$alkoxy,
(4) $C_{1-6}$alkylthio,
(5) OH,
(6) CN,
(7) $CF_3$,
(8) $CO_2R^7$, and
(9) $C_{0-6}$alkyl-W—$NO_S$;
each Rb is independently selected from the group consisting of:
(1) $C_{1-6}$alkyl, optionally substituted with 1–3 halo groups or optionally substituted with phenyl, naphthyl or $HET^4$, each of said phenyl, naphthyl or $HET^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and
(2) phenyl, naphthyl or $HET^5$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;
$R^7$ and $R^8$ is selected from the group consisting of
(a) hydrogen and
(b) $C_{1-6}$alkyl; and
$HET^4$ and $HET^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

Another embodiment of the invention encompasses a compound of Formula II

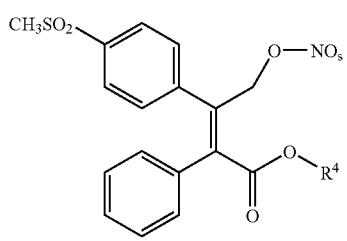

or a pharmaceutically acceptable salt thereof, wherein
$R^4$ is selected from the group consisting of:
(a) $C_{1-6}$alkyl, optionally substituted with 1–3 halo groups or optionally substituted with phenyl, naphthyl or $HET^1$, each of said phenyl, naphthyl or $HET^1$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
(b) phenyl, naphthyl or $HET^2$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
$R^6$ is selected from the group consisting of
(a) hydrogen and
(b) $C_{1-6}$alkyl;
s is 1 or 2; and
$HET^1$ and $HET^2$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

Another embodiment of the invention encompasses a compound of Formula II wherein $R^4$ is methyl, ethyl, propyl or isopropyl.

Another embodiment of the invention encompasses a compound of Formula II wherein
$R^4$ is phenyl or benzyl, wherein said phenyl and the phenyl portion of said benzyl are each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$; and
$R^6$ is selected from the group consisting of
  (a) hydrogen and
  (b) $C_{1-6}$alkyl.

Another embodiment of the invention encompasses a compound of Formula I wherein s is 2.

Another embodiment of the invention encompasses a compound of Formula III

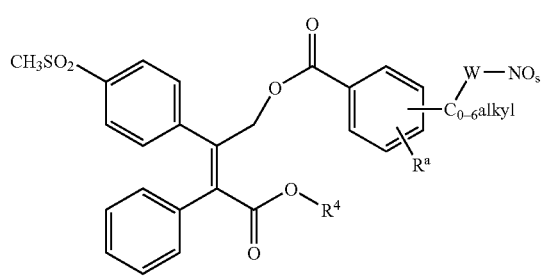

III or a pharmaceutically acceptable salt thereof, wherein
$R^4$ is selected from the group consisting of:
  (a) $C_{1-6}$alkyl, optionally substituted with 1–3 halo groups or optionally substituted with phenyl, naphthyl or $HET^1$, each of said phenyl, naphthyl or $HET^1$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
  (b) phenyl, naphthyl or $HET^2$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
$R^6$ is selected from the group consisting of
  (a) hydrogen,
  (b) $C_{1-6}$alkyl;
$R^a$ is hydrogen or $C_{0-6}$alkyl-W—$NO_s$.
each s is independently 1 or 2,
each W is independently selected from the group consisting of:

(1) oxygen,
  (2) sulfur,
  (3) 
$$-\underset{\underset{CO_2R^b}{|}}{\overset{\overset{CO_2R^b}{|}}{C}}-$$

(4)
$$-\underset{\underset{R^b}{|}}{\overset{\overset{O}{\|}}{C}}-\underset{\underset{R^b}{|}}{\overset{\overset{CO_2R^b}{|}}{C}}-$$

each $R^b$ is independently selected from the group consisting of:
  (1) $C_{1-6}$alkyl, optionally substituted with 1–3 halo groups or optionally substituted with phenyl, naphthyl or $HET^4$, each of said phenyl, naphthyl or $HET^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and
  (2) phenyl, naphthyl or $HET^5$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;
$R^8$ is selected from the group consisting of
  (a) hydrogen,
  (b) $C_{1-6}$alkyl; and
$HET^1$, $HET^2$, $HET^4$ and $HET^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

Another embodiment of the invention encompasses a compound of Formula III wherein $R^4$ is methyl, ethyl, propyl or isopropyl.

Another embodiment of the invention encompasses a compound of Formula III wherein
$R^4$ is phenyl or benzyl, wherein said phenyl and the phenyl portion of said benzyl are each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$; and
$R^6$ is selected from the group consisting of
  (a) hydrogen and
  (b) $C_{1-6}$alkyl.

Another embodiment of the invention encompasses a compound of Formula III wherein s is 2 and W is oxygen.

Another embodiment of the invention encompasses a compound of Formula III wherein $R^a$ is

—$CH_2$—W—$NO_S$.

Another embodiment of the invention encompasses a compound of Formula IV

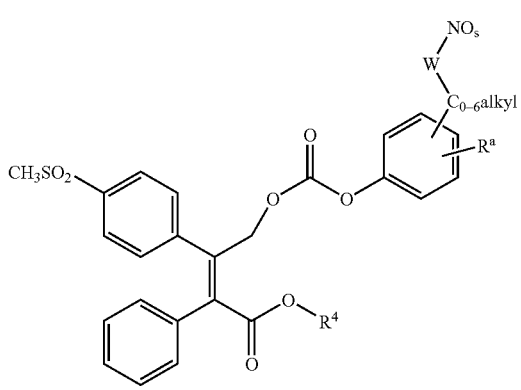

or a pharmaceutically acceptable salt thereof, wherein
$R^4$ is selected from the group consisting of:
  (a) $C_{1-6}$alkyl, optionally substituted with 1–3 halo groups or optionally substituted with phenyl, naphthyl or $HET^1$, each of said phenyl, naphthyl or $HET^1$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
  (b) phenyl, naphthyl or $HET^2$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
$R^6$ is selected from the group consisting of
  (a) hydrogen,
  (b) $C_{1-6}$alkyl;
$R^a$ is hydrogen or $C_{0-6}$alkyl-W—$NO_S$.
each s is independently 1 or 2;
each W is independently selected from the group consisting of:

(1) oxygen,
  (2) sulfur,
  (3) 
$$-\underset{\underset{CO_2R^b}{|}}{\overset{\overset{CO_2R^b}{|}}{C}}-$$
  (4) 
$$-\underset{\underset{R^b}{|}}{\overset{\overset{O}{\|}}{C}}-\underset{\underset{R^b}{|}}{\overset{\overset{CO_2R^b}{|}}{C}}-$$

each $R^b$ is independently selected from the group consisting of:
  (1) $C_{1-6}$alkyl, optionally substituted with 1–3 halo groups or optionally substituted with phenyl, naphthyl or $HET^4$, each of said phenyl, naphthyl or $HET^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and
  (2) phenyl, naphthyl or $HET^5$; each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;
$R^8$ is selected from the group consisting of
  (a) hydrogen,
  (b) $C_{1-6}$alkyl; and
$HET^1$, $HET^2$, $HET^4$ and $HET^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

Another embodiment of the invention encompasses a compound of Formula IVa

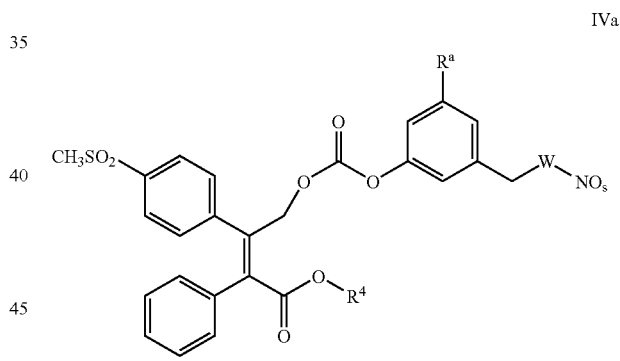

or a pharmaceutically acceptable salt thereof, wherein
$R^4$ is selected from the group consisting of:
  (a) $C_{1-6}$alkyl, optionally substituted with 1–3 halo groups or optionally substituted with phenyl, naphthyl or $HET^1$, each of said phenyl, naphthyl or $HET^1$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
  (b) phenyl, naphthyl or $HET^2$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
$R^6$ is selected from the group consisting of
  (a) hydrogen,
  (b) $C_{1-6}$alkyl;
$R^a$ is hydrogen or $C_{0-6}$alkyl-W—$NO_S$.
each s is independently 1 or 2;

each W is independently selected from the group consisting of:

(1) oxygen, (2) sulfur, (3) 
```
      CO₂Rᵇ
       |
    —C—
       |
      CO₂Rᵇ,
```

(4)
```
      O    CO₂Rᵇ
      ||    |
    —C—C—
            |
            Rᵇ
``` each Rb is independently selected from the group consisting of:
 (1) $C_{1-6}$alkyl, optionally substituted with 1–3 halo groups or optionally substituted with phenyl, naphthyl or $HET^4$, each of said phenyl, naphthyl or $HET^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and
 (2) phenyl, naphthyl or $HET^5$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;

$R^8$ is selected from the group consisting of
 (a) hydrogen,
 (b) $C_{1-6}$alkyl; and $HET^1$, $HET^2$, $HET^4$ and $HET^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

Another embodiment of the invention encompasses a compound of Formula IVa wherein $R^4$ is methyl, ethyl, propyl or isopropyl.

Another embodiment of the invention encompasses a compound of Formula IVa wherein:
$R^4$ is phenyl or benzyl, wherein said phenyl and the phenyl portion of said benzyl are each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$; and $R^6$ is selected from the group consisting of
 (a) hydrogen and
 (b) $C_{1-6}$alkyl.

Another embodiment of the invention encompasses a compound of Formula IVa wherein s is 2 and W is oxygen.

Another embodiment of the invention encompasses a compound of Formula IVa wherein $R^a$ is —$CH_2$—W—$NO_s$.

Another embodiment of the invention encompasses a compound of Formula I wherein $R^4$ is $C_{1-6}$alkyl, monsubstituted with
 (i) $N(R^i)R^{ii}$, wherein $R^i$ and $R^{ii}$ are each independently selected from the group consisting of hydrogen and $C_{1-4}$alkyl or
 (ii) —$CO_2R^{iii}$, wherein $R^{iii}$ is hydrogen or $C_{1-4}$alkyl.

Another embodiment of the invention encompasses a compound selected from the following group:

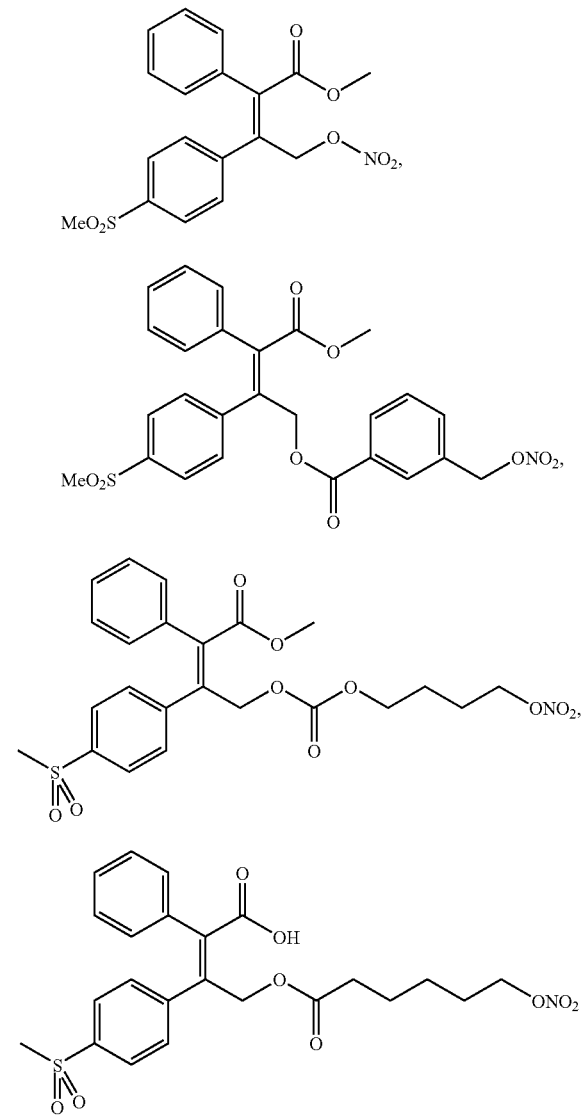

or a pharmaceutically acceptable salt thereof,

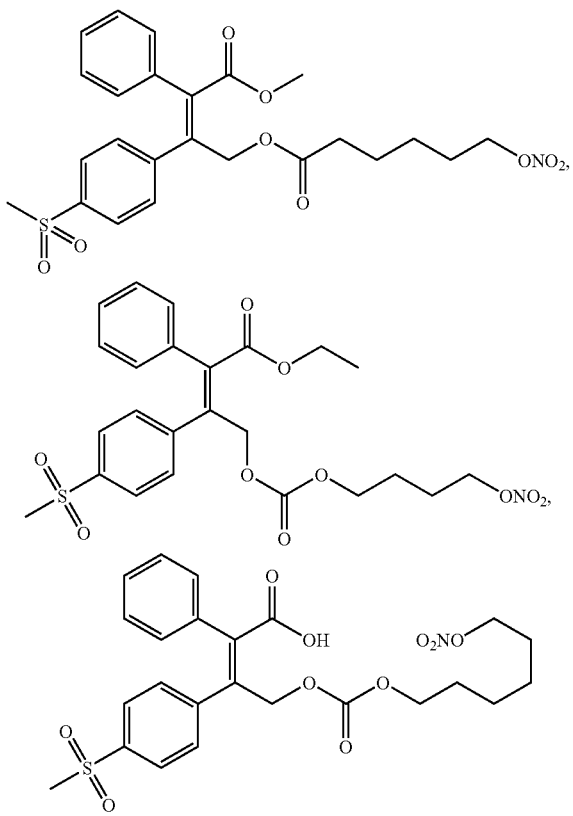
or a pharmaceutically acceptable salt thereof,
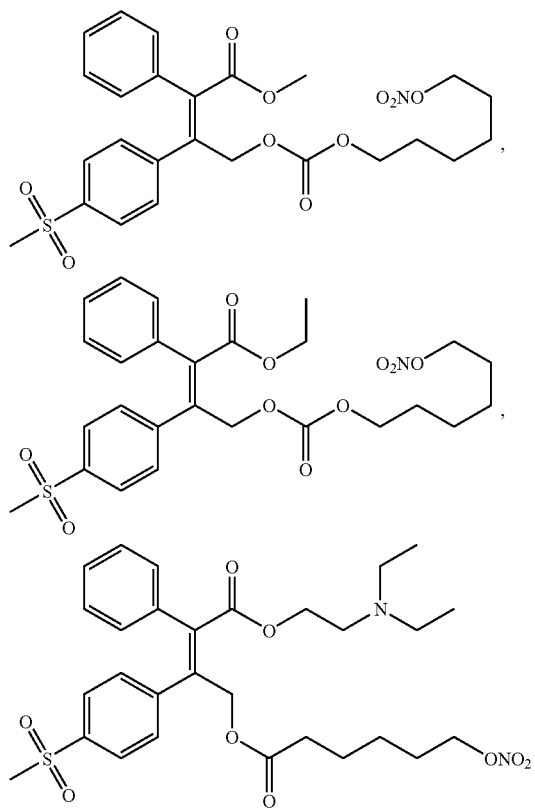
or a pharmaceutically acceptable salt thereof,
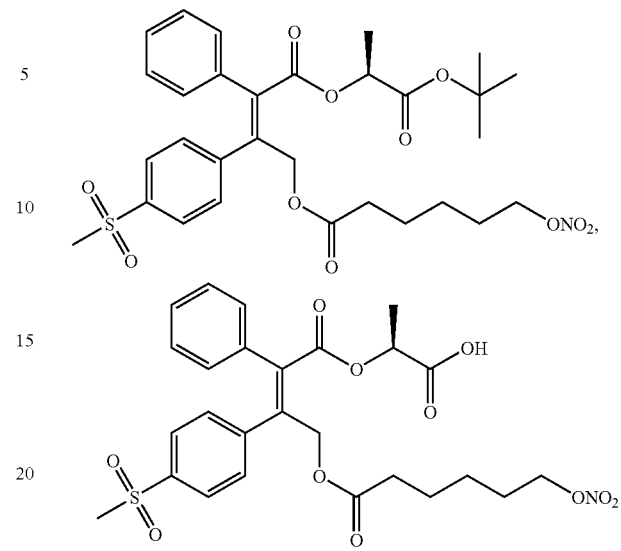
or a pharmaceutically acceptable salt thereof,
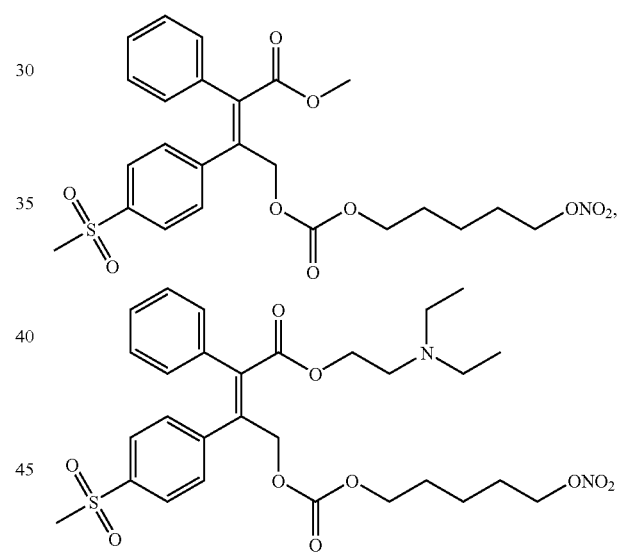
or a pharmaceutically acceptable salt thereof, and
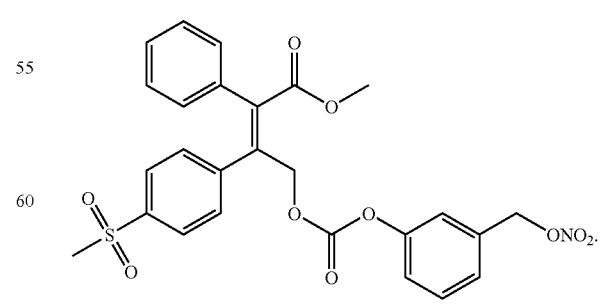
The invention also encompasses a pharmaceutical composition comprising a compound of Formula I and a pharmaceutically acceptable carrier.

The invention also encompasses a method of treating an inflammatory disease susceptible to treatment with a non-steroidal anti-inflammatory agent comprising administering to a patient in need of such treatment of a non-toxic therapeutically effective amount of a compound of Formula I. Within this embodiment is encompassed the above method wherein the patient is also at risk of a thrombotic cardiovascular event.

Another embodiment of the invention encompasses method of treating cyclooxygenase mediated diseases advantageously treated by an active agent that selectively inhibits COX-2 in preference to COX-1 comprising administering to a patient in need of such treatment of a non-toxic therapeutically effective amount of a compound of Formula I. Within this embodiment is encompassed the above method wherein the patient is also at risk of a thrombotic cardiovascular event.

Another embodiment of the invention encompasses a method for treating a chronic cyclooxygenase-2 mediated disease or condition and reducing the risk of a thrombotic cardiovascular event in a human patient in need of such treatment and at risk of a thrombotic cardiovascular event comprising orally concomitantly or sequentially administering to said patient a compound of Formula I in an amount effective to treat the cyclooxygenase-2 mediated disease or condition and aspirin in an amount effective to reduce the risk of the thrombotic cardiovascular event. Within this embodiment is encompassed the above method wherein the compound of Formula I is administered orally on a once daily basis. Within this embodiment is encompassed the above method wherein the compound of Formula I is administered orally on a twice daily basis. Within this embodiment is encompassed the above method wherein the cyclooxygenase-2 selective mediated disease or condition is selected from the group consisting of: osteoarthritis, rheumatoid arthritis and chronic pain. Within this embodiment is encompassed the above method wherein aspirin is administered at a dose of about 30 mg to about 1 g. Within this embodiment is encompassed the above method wherein aspirin is administered at a dose of about 80 to about 650 mg. Within this embodiment is encompassed the above method wherein aspirin is administered at a dose of about 81 mg or about 325 mg. Within this embodiment is encompassed the above method wherein aspirin is orally administered once daily.

The invention also encompasses a pharmaceutical composition comprising a compound of Formula I and aspirin in combination with a pharmaceutically acceptable carrier.

For purposes of this specification alkyl is defined to include linear, branched, and cyclic structures, with $C_{1-6}$alkyl including including methyl, ethyl, propyl, 2-propyl, s- and t-butyl, butyl, pentyl, hexyl, 1,1-dimethylethyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$alkylthio is intended to include alkylthio groups of from 1 to 6 carbon atoms of a straight, branched or cyclic configuration. Examples of lower alkylthio groups include methylthio, propylthio, isopropylthio, cycloheptylthio, etc. By way of illustration, the propylthio group signifies —$SCH_2CH_2CH_3$.

Some of the compounds described herein contain olefinic double bonds, and unless specified otherwise, are meant to include both E and Z geometric isomers.

The term "treating a chronic cylcooxygenase-2 mediated disease or condition" means treating or preventing any chronic disease or condition that is advantageously treated or prevented by inhibiting the cyclooxygenase-2 enzyme. The term includes the relief of pain, fever and inflammation of a variety of conditions including rheumatic fever, symptoms associated with influenza or other viral infections, common cold, low back pain, neck pain, dysmenorrhea, headache, migraine, toothache, sprains and strains, myositis, neuralgia, synovitis, arthritis, including rheumatoid arthritis, degenerative joint diseases (osteoarthritis), gout, ankylosing spondylitis, bursitis, burns, injuries, and pain and inflammation following surgical procedures. In addition, such a compound may inhibit cellular neoplastic transformations and metastatic tumor growth and hence can be used in the treatment and/or prevention of cancer. In addition, such a compound may inhibit the onset or progression of Altzheimer's disease or cognitive impairment. The term also includes the treatment and/or prevention of cyclooxygenase-mediated proliferative disorders such as may occur in diabetic retinopathy and tumor angiogenesis. The term "treating" encompasses not only treating a patient to relieve the patient of the signs and symptoms of the disease or condition but also prophylactically treating an asymptomatic patient to prevent the onset or progression of the disease or condition.

A "thrombotic cardiovascular event" is defined as any sudden event of a type known to be caused by platelet aggregation, thrombosis, and subsequent ischemic clinical events, including thrombotic or thromboembolic stroke, myocardial ischemia, myocardial infarction, angina pectoris, transient ischemic attack (TIA; amaurosis fugax), reversible ischemic neurologic deficits, and any similar thrombotic event in any vascular bed (splanchnic, renal, aortic, peripheral, etc.).

The term "patient in need of such treatment and at risk of a thrombotic cardiovascular event" means a patient in need of both treatment for a cyclooxygenase-2 mediated disease and also at risk of a thrombotic cardiovascular event. One skilled in the art can diagnose a patient that is in need of treatment for a cyclooxygenase-2 mediated disease or condition and also at risk of suffering a thrombotic cardiovascular event. For example, such a patient may be over the age of 50 with osteoarthritis and with a previous myocardial infarction. Other risk factors for a thrombotic cardiovascular event include hypertension, hypercholesterolemia, diabetes mellitus, chronic renal impairment, smoking, and any prior personal or family history of such an event. Administration of the drug combination to the patient includes both self administration and administration to the patient by another person.

The terms "nitric oxide releasing-cyclooxygenase-2 selective inhibitor," "NO-cyclooxygenase-2 selective inhibitor," "nitric oxide releasing-COX-2 inhibitor" and "NO-COX-2 inhibitor" mean a modified version of a cycloxygenase-2 selective inhibitor or a prodrug as defined above linked to a NO releasing moiety by means of a linking group such as an ester linkage.

The term "amounts that are effective to treat" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician. The inhibitor of cyclooxygenase-2 may be administered at a dosage level up to conventional dosage levels for NSAIDs. Suitable dosage levels will depend upon the antiinflammatory effect of the chosen inhibitor of cyclooxygenase-2, but typically suitable levels will be about 0.001 to 50 mg/kg per day, preferably 0.005 to 30 mg/kg per day, and especially 0.05 to 10 mg/kg per day. The compound may be administered on a regimen of once or twice per day.

The term "amount effective to reduce the risk of" means the amount of a pharmaceutical drug that will prevent or reduce the risk of occurrence of the biological or medical event that is sought to be prevented in a tissue, a system, animal or human by a researcher, veterinarian, medical doctor or other clinician. Aspirin is administered at a dose of about 30 mg to about 1 g once daily, preferably at a dose of about 80 mg to about 650 mg.

The term "concomitantly administering" means administering the agents substantially concurrently. The term "concomitantly administering" encompasses not only administering the two agents in a single pharmaceutical dosage form but also the administration of each active agent in its own separate pharmaceutical dosage formulation. Where separate dosage formulations are used, the agents can be administered at essentially the same time, i.e., concurrently.

The term "sequentially administering" means administering the agents at separately staggered times. Thus, agents can be sequentially administered such that the beneficial pharmaceutical effect of NO-aspirin and the COX-2 inhibitor or aspirin and the NO-COX-2 inhibitor are realized by the patient at substantially the same time. Thus, for example, if a COX-2 selective inhibitor and NO releasing aspirin are both administered on a once a day basis, the interval of separation between sequential administration of the two agents can be up to twelve hours apart.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

The Compound of Formula I is useful for the relief of pain, fever and inflammation of a variety of conditions including rheumatic fever, symptoms associated with influenza or other viral infections, common cold, low back and neck pain, dysmenorrhea, headache, migraine, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compounds of Formula I may also be useful for the treatment of dementia including pre-senile and senile dementia, and in particular, dementia associated with Alzheimer Disease (i.e. Alzheimer's dementia).

Compounds of Formula I will also inhibit prostanoid-induced smooth muscle contraction by preventing the synthesis of contractile prostanoids and hence may be of use in the treatment of dysmenorrhea, premature labor and asthma. They will also be useful to inhibit bone loss (osteoporosis).

By virtue of its high cyclooxygenase-2 (COX-2) activity and/or its selectivity for cyclooxygenase-2 over cyclooxygenase-1 (COX-1) as defined above, compounds of Formula I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (e.g. impaired renal function); those prior to surgery or taking anticoagulants; and those susceptible to NSAID induced asthma.

Similarly, compounds of Formula I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.

Compounds of the present invention are inhibitors of cyclooxygenase-2 and are thereby useful in the treatment of cyclooxygenase-2 mediated diseases as enumerated above. This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ (PGE$_2$) synthesized in the presence of arachidonic acid, cyclooxygenase-1 or cyclooxygenase-2 and a compound of Formula I. The IC$_{50}$ values represent the concentration of inhibitor required to return PGE$_2$ synthesis to 50% of that obtained as compared to the uninhibited control. For the treatment of any of these cyclooxygenase mediated diseases, compounds of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethy-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.) Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Methods of Synthesis

Stilbene derivatives useful as cyclooxygenase-2 selective inhibitors are disclosed in U.S. Pat. No. 5,849,943, which is hereby incorporate by reference in its entirety.

The compounds of the present invention can be prepared according to the following methods:

Method A-1

Treatment of a phenyl acetic with iPrMgCl in THF followed by the addition of acetophenone yields the corresponding aldol adducts. Esterification followed by dehydration results in the formation of the substituted stilbene iv. Conversion of the para-bromide substituent of iv to, for example, a methylsulfone can be accomplished by treatment with methanesulfinic acid sodium salt with CuI in NMP. Subsequent bromination of the allylic methyl group in v can be accomplished using standard conditions such as NBS with $Bz_2O_2$ in $CCl_4$. Introduction of the nitrate functional group is accomplished through the action of $AgNO_3$ in a suitable solvent such as acetonitrile. Alternatively, the intermediate bromide can be displaced with a carboxylate salt to yield the corresponding ester such as ix. Introduction of the nitrate in this case can be accomplished by, for example, deprotection of a primary silyl ether, conversion of the liberated alcohol into a bromide followed by treatment with $AgNO_3$ to deliver compounds such a x.

METHOD A-1

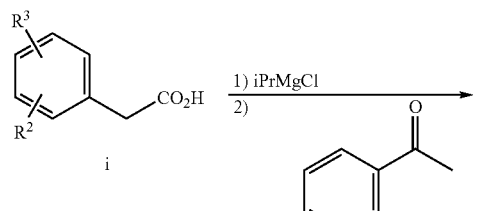

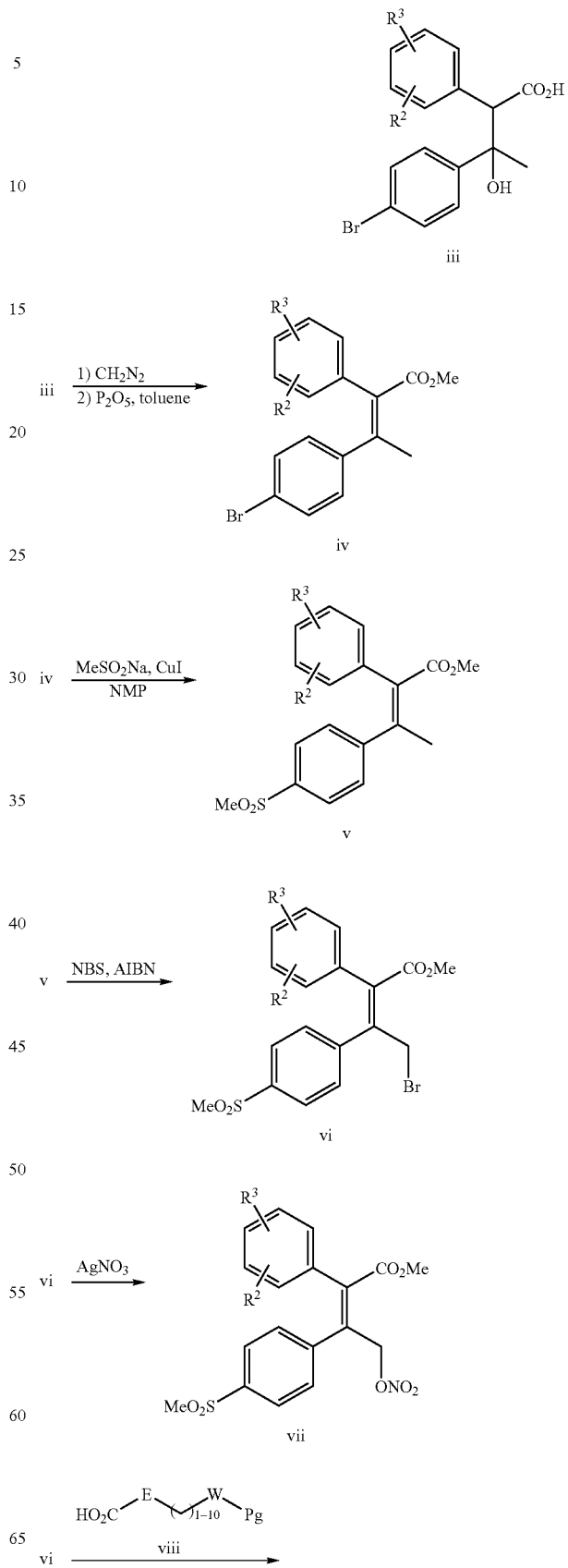

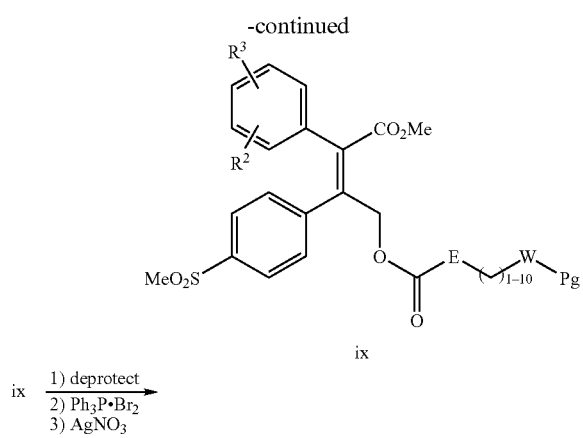

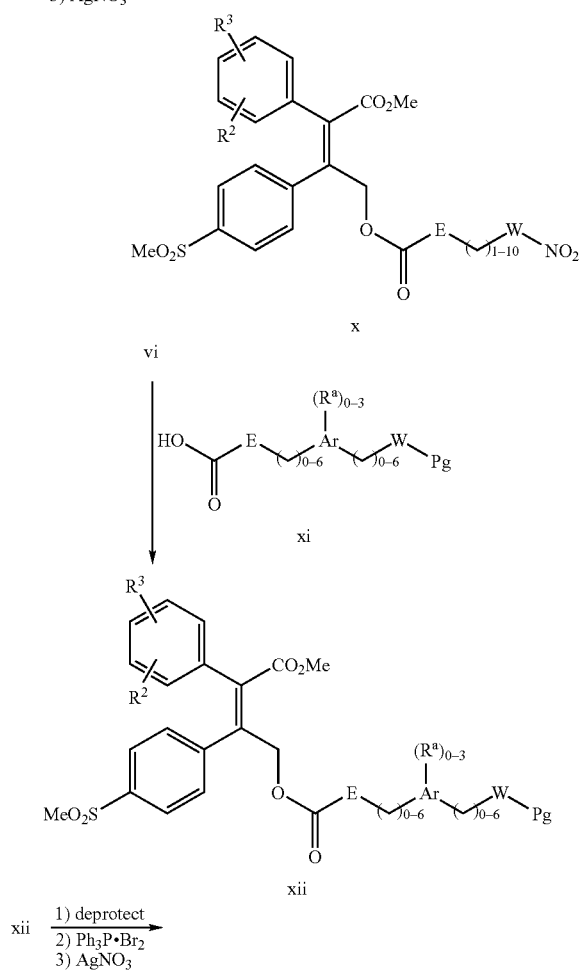

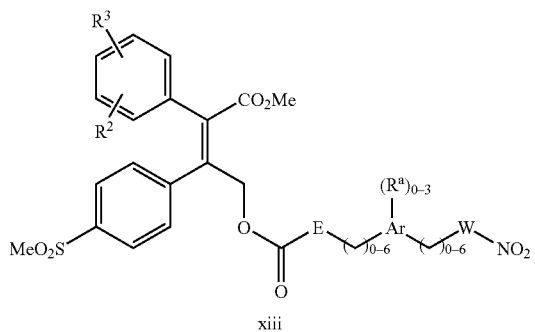

Method A-2:

Diphenyl lactone xiv is reduced to the corresponding diol xv by a suitable reducing agent such as diisobutyl aluminum hydride in an appropriate solvent such as toluene, hexane, tetrahydro-furan or ether. The diol xv can be acylated with a variety of agents such as acid chlorides, chloroformates or ethyl esters to yield products such as xvii. Oxidation of the primary alcohol can be accomplished using; for example, a two step procedure by first oxidizing to the aldehyde with Dess-Martin reagent in $CH_2Cl_2$ followed by further oxidation with the using of sodium chlorite. Subsequent esterification can be realized by mixing the carboxylic acid with an alcohol (R4OH) with an appropriate dehydrating agent such as DCC or EDCI. Introduction of the nitrate moiety follows the protocol described in Method A-1.

METHOD A-2

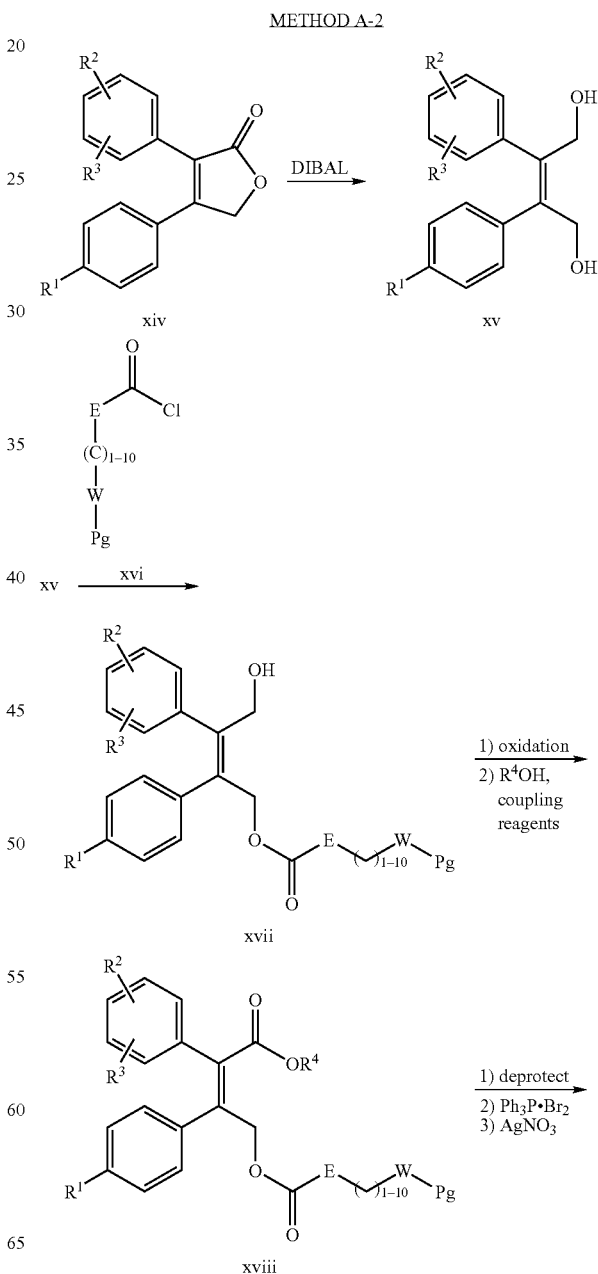

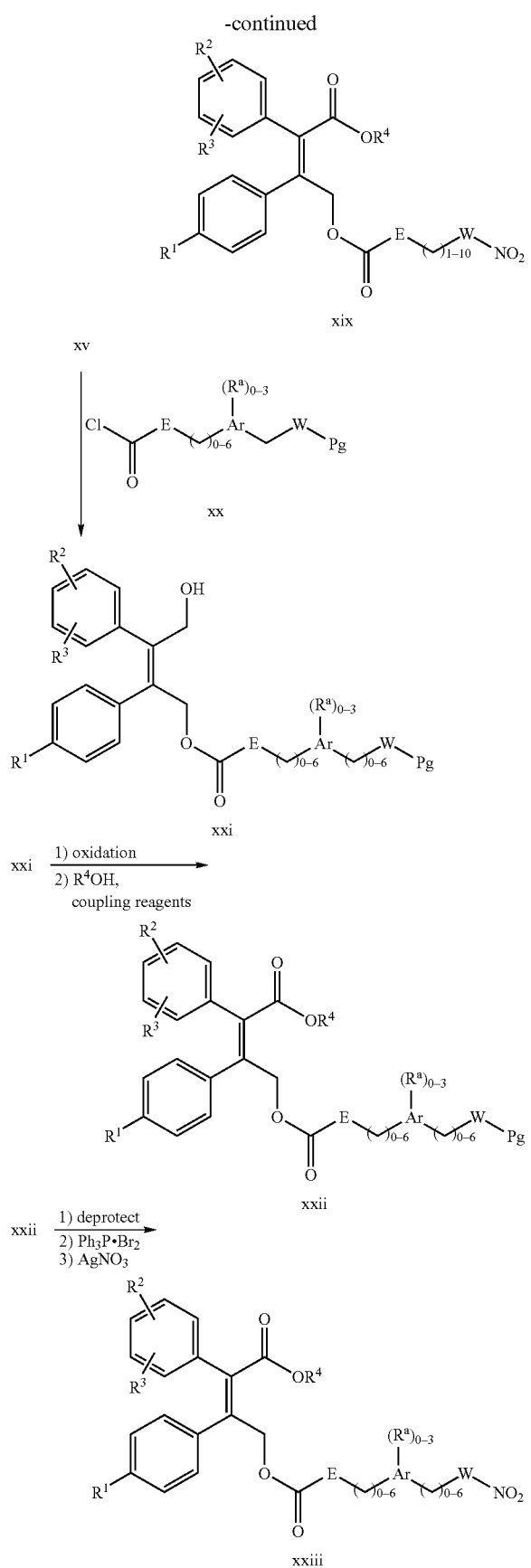

Method A-3:

A diphenyl maleic anhydride 18 can be reduced to diol xv with suitable hydride reducing agents such as di-isobutyl aluminum hydride or lithium aluminum hydride. Solvents such as toluene, tetrahydrofuran or ether, or a mixture thereof are suitable for the reduction.

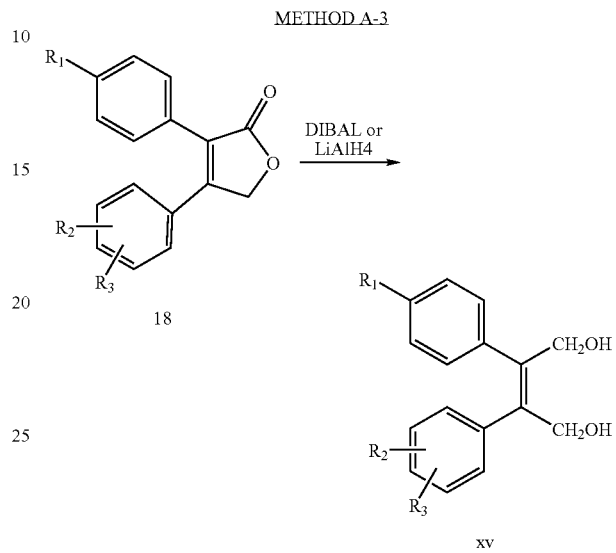

In Table I are shown some lactones xiv from which the compounds of the present invention can be prepared. Methods for making these lactones are well known in the art. For example, see the following patents and printed publications, all of which are hereby incorporated by reference in their entirety: U.S. Pat. No. 5,474,995, granted Dec. 12, 1995; WO 95/00501, published Jan. 5, 1995; U.S. Pat. No. 5,585,504, granted Dec. 17, 1996; WO 96/08482, published Mar. 21, 1996; U.S. Pat. No. 5,786,515, granted Jul. 28, 1998; WO 97/10195, published Mar. 20, 1997; U.S. Pat. No. 5,840,924, granted Nov. 24, 1998; and WO 98/00416, published Jan. 8, 1998.

TABLE I

| | Lactone |
|---|---|
| 1 | (structure with phenyl and 4-S(O)₂Me phenyl furanone) |
| 2 | (structure with 4-F phenyl and 4-S(O)₂NH₂ phenyl furanone) |

TABLE I-continued

| Structure | Lactone |
|---|---|
| 3-(2,4-difluorophenyl)-4-[4-(methylsulfonyl)phenyl]furan-2(5H)-one | 3 |
| 3-(3,4-difluorophenyl)-4-[4-(methylsulfonyl)phenyl]furan-2(5H)-one | 4 |
| 3-(2,6-difluorophenyl)-4-[4-(methylsulfonyl)phenyl]furan-2(5H)-one | 5 |
| 3-(2,5-difluorophenyl)-4-[4-(methylsulfonyl)phenyl]furan-2(5H)-one | 6 |
| 3-(3,5-difluorophenyl)-4-[4-(methylsulfonyl)phenyl]furan-2(5H)-one | 7 |
| 3-(4-bromophenyl)-4-[4-(methylsulfonyl)phenyl]furan-2(5H)-one | 8 |
| 3-(4-chlorophenyl)-4-[4-(methylsulfonyl)phenyl]furan-2(5H)-one | 9 |
| 3-(4-methoxyphenyl)-4-[4-(methylsulfonyl)phenyl]furan-2(5H)-one | 10 |
| 3-(4-fluorophenyl)-4-[4-(methylsulfonyl)phenyl]furan-2(5H)-one | 11 |
| 3-(2-chlorophenyl)-4-[4-(methylsulfonyl)phenyl]furan-2(5H)-one | 12 |
| 3-(2-bromo-4-fluorophenyl)-4-[4-(methylsulfonyl)phenyl]furan-2(5H)-one | 13 |
| 3-(2-bromo-4-chlorophenyl)-4-[4-(methylsulfonyl)phenyl]furan-2(5H)-one | 14 |

TABLE I-continued
| | Lactone |
|---|---|
| 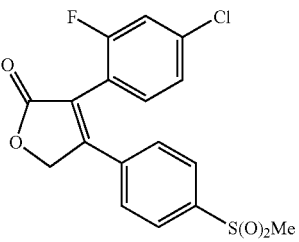 | 15 |
| 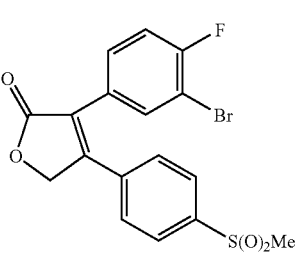 | 16 |
| 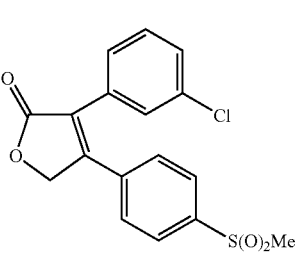 | 17 |
| 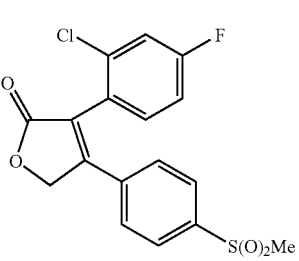 | 18 |
| 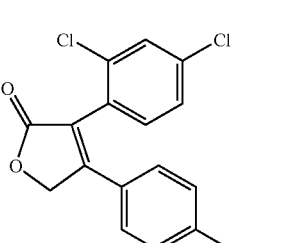 | 19 |
| 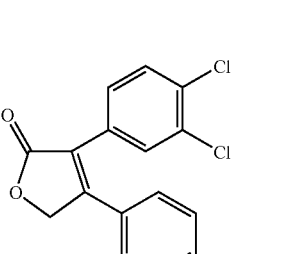 | 20 |
| 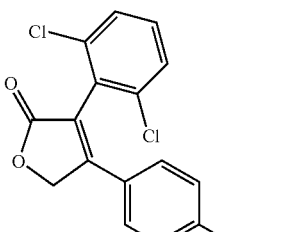 | 21 |
| 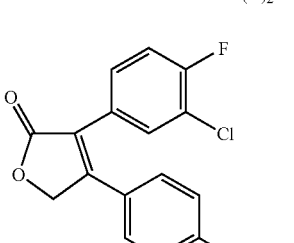 | 22 |
| 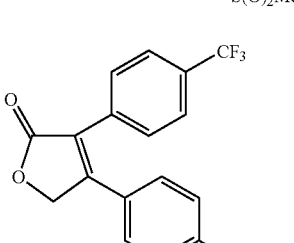 | 23 |
| 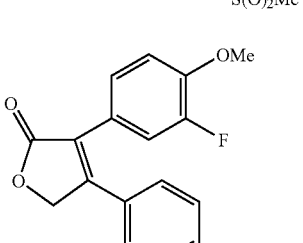 | 24 |
| 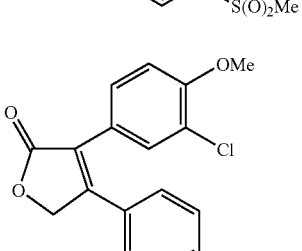 | 25 |
| 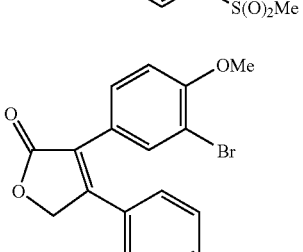 | 26 |

TABLE I-continued

| Structure | Lactone |
|---|---|
| 3-(2-fluorophenyl)-4-(4-methylsulfonylphenyl) furanone | 27 |
| 3-(4-methylthiophenyl)-4-(4-methylsulfonylphenyl) furanone | 28 |
| 3-(3-fluorophenyl)-4-(4-methylsulfonylphenyl) furanone | 29 |
| 3-(2-chloro-6-fluorophenyl)-4-(4-methylsulfonylphenyl) furanone | 30 |
| 3-(3-bromo-4-methylphenyl)-4-(4-methylsulfonylphenyl) furanone | 31 |
| 3-(4-bromo-2-fluorophenyl)-4-(4-methylsulfonylphenyl) furanone | 32 |
| 3-(3,4-dibromophenyl)-4-(4-methylsulfonylphenyl) furanone | 33 |
| 3-(4-chloro-3-fluorophenyl)-4-(4-methylsulfonylphenyl) furanone | 34 |
| 3-(4-bromo-3-fluorophenyl)-4-(4-methylsulfonylphenyl) furanone | 35 |
| 3-(4-bromo-2-chlorophenyl)-4-(4-methylsulfonylphenyl) furanone | 36 |
| 3-(3,4-dichlorophenyl)-4-(4-sulfamoylphenyl) furanone | 37 |
| 3-(3,4-difluorophenyl)-4-(4-sulfamoylphenyl) furanone | 38 |

TABLE I-continued

| | Lactone |
|---|---|
| (structure: 4-OMe, 3-Cl phenyl / 4-S(O)₂NH₂ phenyl lactone) | 39 |
| (structure: 4-OMe, 3-Br phenyl / 4-S(O)₂NH₂ phenyl lactone) | 40 |
| (structure: 4-S(O)₂NH₂ phenyl / phenyl lactone) | 41 |
| (structure: 4-F phenyl / 4-S(O)₂NH₂ phenyl lactone) | 42 |
| (structure: 4-S(O)₂NH₂ phenyl / 2,4-di-F phenyl lactone) | 43 |
| (structure: 4-S(O)₂NH₂ phenyl / 4-Cl phenyl lactone) | 44 |
| (structure: 4-S(O)₂NH₂ phenyl / 2,4-di-Cl phenyl lactone) | 45 |
| (structure: 4-S(O)₂NH₂ phenyl / 4-Br phenyl lactone) | 46 |
| (structure: 4-S(O)₂NH₂ phenyl / 2-F, 4-Br phenyl lactone) | 47 |

Assays for Determining Biological Activity

The compounds of Formula I may be tested using the following assays to determine their biological activity.

Inhibition of Cyclooxygenase Activity

Compounds are tested as inhibitors of cyclooxygenase activity in whole cell and microsomal cyclooxygenase assays. Both of these assays measure prostaglandin $E_2$ ($PGE_2$) synthesis in response to arachidonic acid, using a radioimmunoassay. Cells used for whole cell assays, and from which microsomes are prepared for microsomal assays, are human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate addition. $IC_{50}$ values represent the concentration of putative inhibitor required to return $PGE_2$ synthesis to 50% of that obtained as compared to the uninhibited control.

1. Microsomal Cyclooxygenase Assay

Cox microsomal fractions are prepared as previously described (Percival et al., Arch. Biochem. Biophys. (1994) 315:111–118). The enzyme reactions are performed in 50 mM KPi pH 8.0, 1 µM heme, 1 mM phenol supplemented with 10 µg/ml of each Cox-1 or Cox-2 microsomal fractions. 1 µl DMSO or test compound (100 fold stock concentrated in DMSO) are added to 100 µl buffer. The enzyme reaction is initiated 15 minutes later by the addition of 10 µl of 100 µM arachidonic acid. The enzyme reaction is allowed to proceed for 5 minutes at room temperature before being stopped by the addition of 101 µl 1 N HCl. $PGE_2$ levels are then determined by EIA (Assay Designs) using the manufacturer's instruction.

By way of example, Example 9 gave $IC_{50}$ values of >100 µM against both microsomal human COX-1 and COX-2. This demonstrates that the unconverted prodrug is inactive against both COX-1 and COX-2.

Human Whole Blood Cyclooxygenase Assay

Assays are performed as described in Brideau et al. (1996) Inflammation Res. 45:68–74 and as summarized below.

1. COX-2 (LPS-Induced $PGE_2$ Production):

Fresh blood is collected in heparinized tubes by venipuncture from healthy male volunteers. These subjects had no apparent inflammatory conditions and had not taken any NSAIDs for at least 7 days prior to blood collection. The blood is initially pre-incubated with bacterial lipopolysaccharide (LPS) at 100 µg/ml (Sigma Chem, #L-2630 from E. coli, serotype 0111:B4; diluted in 0.1% w/v bovine serine albumin in phosphate buffered saline). Five minutes later, 500 µL aliquots of the LPS-treated blood are incubated with either 2 µL vehicle (DMSO) or 2 µL of test compound in DMSO for 24 h at 37° C. (for induction of COX-2). Unstimulated control blood at time zero (no LPS) is used as blank. At the end of the 24 h incubation, the blood is centrifuged at 3,000 rpms for 10 min at 4° C. to obtain plasma. The plasma is assayed for $PGE_2$ using an enzyme immunoassay kit (Assay Designs, 901-001) according to the manufacturer's instructions.

2. COX-1 (Clotting-Induced $TXB_2$ Production):

Fresh blood from male or female volunteers is collected into vacutainers containing no anticoagulants. These subjects have no apparent inflammatory conditions and have not taken any NSAIDs for at least 7 days prior to blood collection. Aliquots of 500 µL are immediately transferred to polypropylene tubes preloaded with 2 µL of either DMSO or 2 µL of test compound in DMSO. The tubes are vortexed and incubated at 37° C. for 1 h to allow the blood to clot. At the end of the incubation, serum is obtained by centrifugation (3,000 rpms for 10 min at 4° C.). The serum is obtained and is assayed for $TXB_2$ using an enzyme immunoassay kit (Assay Designs, 901-002) according to the manufacturer's instructions.

Results

Using the above assay, it can be demonstrated that the compounds of the invention have a COX-2 potency and COX-2/COX-1 selectivity comparable to rofecoxib and thus, the prodrug compounds of the invention convert in vivo to rofecoxib.

Representative Rat Paw Edema Assay—Protocol

Male Sprague-Dawley rats (150–200 g) are fasted overnight and are given p.o., either vehicle (1% methocell) or a test compound in the morning. One hr later, a line drawn using a permanent marker at the level above the ankle in one hind paw to define the area of the paw to be monitored. The paw volume ($V_{Oh}$) is measured using a plethysmometer (Ugo-Basile, Italy) based on the principle of water displacement. The animals are then injected subplantarly with 50 ul of a 1% carrageenan solution in saline (sigma Chem) into the paw using an insulin syringe with a 25-gauge needle (i.e. 500 ug carrageenan per paw). Three hr later, the paw volume ($V_{3h}$) is measured and the increases in paw volume ($V_{3h}-V_{Oh}$) are calculated. Paw edema data are the compared with the vehicle-control group and percent inhibitions calculated taking the values in the control group as 100%. All treatment groups are coded to eliminate observer bias.

By way of example, the results of the above assay for Example 3 are as follows:

| dose (mg/kg) | Paw Edema (% inhibition) |
|---|---|
| 1 | 42 |
| 3 | 51 |
| 10 | 68 |
| 30 | 79 |

Acute Gastric Erosion Model in Rats

The gastric protective effects of the compounds of the present invention co-administration with aspirin may be evaluated in the following assay.

Male Wistar rats (200–250 g) were fasted for 16–18 h prior to use for experiment. Aspririn, rofecoxib in combination with aspirin (dosed separately), or test compound in combination with aspirin (dosed separately) were given on the morning of the experiment at a dosing volume of 1 ml/kg in 0.5% methocel. Three hr later, the animals were euthanized by $CO_2$ inhalation and the stomach removed, rinsed in saline and prepared for imaging processing. Microscopic pictures of the stomach were taken using a digital camera and gastric erosions were measured using an imaging software by an observer unaware of the treatment groups. The length of gastric erosions was measured in mm and the total length of all erosions from each stomach was obtained and used as gastric damage score.

This model is also described in S. Fiorucci, et al., Gastroenterology, vol. 123, pp. 1598–1606, 2002 and M. Souza, et al., Am. J. Physiol. Gastrointest. Liver Physiol., vol. 285, pp. G54–G61, 2003.

NSAID-Induced Gastropathy in Rats

Rationale

The major side effect of conventional NSAIDs is their ability to produce gastric lesions in man. Rats are sensitive to the actions of NSAIDs and have been used commonly in the past to evaluate the gastrointestinal side effects of current conventional NSAIDs. In the present assay, NSAID-induced gastrointestinal damage is observed by measuring urinary $^{51}Cr$ excretion after oral dosing of $^{51}Cr$-EDTA. Urinary $^{51}Cr$ excretion is a well-established and sensitive technique to detect gastrointestinal integrity in animals and man.

Methods

Male Sprague-Dawley rats (150–200 g) are administered orally a test compound either once (acute dosing) or in multiple doses for a few days (chronic dosing). Immediately after the administration of the last dose, the rats are given an oral dose of $^{51}Cr$-EDTA (10 µCi/rat). The animals are placed individually in metabolism cages with food and water ad lib. Urine is collected for a 24 hr period and $^{51}Cr$ urinary excretion is calculated as a percent of total ingested dose.

Protein-Losing Gastrophathy in Squirrel Monkeys

Rationale

Protein-losing gastropathy (manifested as appearance of circulating cells and plasma proteins in the GI tract) is a significant and dose-limiting adverse response to NSAIDs. This can be quantitatively assessed by intravenous administration or $^{51}CrCl_3$ solution. This isotopic ion can avidly bind to cell and serum globins and cell endoplasmic reticulum. Measurement of radioactivity appearing in feces collected for 24 hr after administration of the isotope thus provides a sensitive and quantitative index of protein-losing gastropathy.

Methods

Groups of male squirrel monkeys (0.8 to 1.4 kg) are treated by gavage with 1% methocel or a test compounds at multiple doses for a few days. Intravenous $^{51}$Cr (5 µCi/kg in 1 ml/kg PBS) is administered 1 hr after the last drug/vehicle dose, and feces collected for 24 hr in a metabolism cage and assessed for excreted $^{51}$Cr by gamma-counting. $^{51}$Cr fecal excretion is calculated as a percent of total injected dose.

Rat Aortic Smooth Muscle Rings in Male Spargue-Dawley Rats

Preparation of Rat Aortic Smooth Muscle Rings

Male Sprague-Dawley rats (Charles River Laboratories (Wilmington, Mass.) are euthanized by intraperiton injection of a high dose of sodium pentobarbitone (80–100 mg/kg). The thoracic aorta is rapidly excised and immediately placed in a Petri dish containing warm (37° C.) oxygenated (95% 0, and 5% $CO_2$) Kreb's buffer (composition per millimolar: NaCl (119); KCl (4.69); $CaCl_2.H_2O$ (2.52); $MgSO_4.7H_2O$ (0.57); $NaHCO_2$, (25); $NaH_2PO_4.H_2O$ (1.01) and glucose (11.1)}. Under a stereoscopic dissecting microscope, the aorta is cleaned, freed from adhering fat and connective tissues. The tissue is cut into ring segments, each approximately 2–3 mm in length.

For experiments to measure relaxation of the tissue under various conditions, a stainless steel tissue holder and a U-shaped stainless steel wire are inserted into the lumen of the aortic ring. The tissue holder anchored the ring at the bottom of the organ bath whereas the end of the U-shaped steel wire is tied with fine silk thread so that it connected to the FT-202 transducer. The tissue holder and the steel wire along with the aortic ring are then suspended in a 5-ml, double-jacketed temperature-controlled glass organ bath (Radnoti Glass Technology, Inc., Monrovia, Calif.) filled with fresh Kreb's buffer. A mixture of 95% $O_2$ and 5% $CO_2$ is bubbled through a porous sintered disc at the bottom of the bath. The rings are given an initial resting tension of 1.5 g and the preparation is allowed to equilibrate at the initial tension for about 90 minutes. During this equilibration period, the bath fluid is changed every 15 minutes and replaced with fresh prewarmed (37° C.) Kreb's buffer. The isometric tension of the aortic muscle at rest and its response to different stimuli are recorded on a Power Macintosh 6100 computer via a MacLab 8/S computer interface (CB Sciences, Inc, Milford, Mass.) after an initial amplification through a low-noise ETH-400 bioamplifier (CB Sciences, Inc, Milford, Mass.). Contractile responsiveness of the tissue strips is established with 10 µM phenylephrine, and the strips are incubated with the drug for 20 minutes to establish a steady level of contraction.

To test the relaxation effects, test compounds can be added to the phenylephrine precontracted strips in the tissue bath at cumulative concentrations of 0.1 µM to 0.1 mM. Concentration of test compounds may be increased only after relaxation at the previous concentration had reached a plateau level.

Representative Examples

The invention will now be illustrated by the following non-limiting examples in which, unless stated otherwise:

(i) all operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (IMR) spectrometry or microanalytical data; yields are given for illustration only; when given, NMR data is in the form of delta ($\delta$) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The following abbreviations have the indicated meanings:

| | |
|---|---|
| Ac = | acetyl |
| Bn = | benzyl |
| DBU = | 1,8-diazabicyclo[5.4.0]undec-7-ene |
| DIBAL = | diisobutylaluminum hydride |
| DMAP = | 4-(dimethylamino)pyridine |
| DMF = | N,N-dimethylformamide |
| $Et_3N$ = | triethylamine |
| HBSS = | Hanks' balanced salt solution |
| LDA = | lithium diisopropylamide |
| m-CPBA = | metachloroperbenzoic acid |
| MMPP = | monoperoxyphtalic acid |
| MPPM = | monoperoxyphthalic acid, magnesium salt $6H_2O$ |
| Ms = | methanesulfonyl = mesyl = $S(O)_2Me$ |
| Ms0 = | methanesulfonate = mesylate |
| NSAID = | non-steroidal anti-inflammatory drug |
| OXONE ® = | $2KHSO_5.KHSO_4.K_2SO_4$ |
| PBS = | phosphate buffered saline |
| PCC = | pyridinium chlorochromate |
| PDC = | pyridinium dichromate |
| Ph = | phenyl |
| Phe = | benzenediyl |
| Pye = | pyridinediyl |
| r.t. = | room temperature |
| rac. = | racemic |
| SAM = | aminosulfonyl or sulfonamide or $S(O)_2NH_2$ |
| TBAF = | tetra-n-butylammonium fluoride |
| Th = | 2- or 3-thienyl |
| TFAA = | trifluoroacetic acid anhydride |
| THF = | tetrahydrofuran |
| Thi = | thiophenediyl |
| TLC = | thin layer chromatography |
| TMS-CN = | trimethylsilyl cyanide |
| Tz = | 1H (or 2H)-tetrazol-5-yl |
| $C_3H_5$ = | allyl |

Alkyl Group Abbreviations

| | |
|---|---|
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |

-continued

| c-Pr = | cyclopropyl |
| c-Bu = | cyclobutyl |
| c-Pen = | cyclopentyl |
| c-Hex = | cyclohexyl |

Example 1 methyl (2Z)-3-[4-(methylsulfonyl)phenyl]-4-(nitrooxy)-2-phenylbut-2-enoate

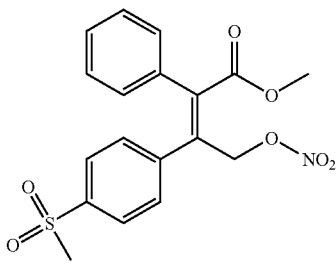

Step 1: methyl (2E)-3-[4-(methylsulfonyl)phenyl]-2-phenylbut-2-enoate

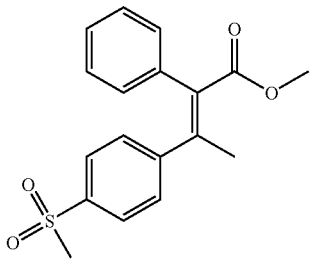

At −78° C., 15 mL of isopropylmagnesium bromide (30 mmol, 2M) was added dropwise to a solution of 15 mmol of phenyl-acetic acid in 4 mL of TBF. The mixture was then warmed to 40° C. and stirred for 30 min and then re-cooled to −78° C. A solution of 15 mmol of 1-(4-methanesulfonyl-phenyl)-ethanone in a minimum amount of THF was added to the reaction mixture. The resulting mixture was warmed again to 40° C. for 30 min, and then the reaction was quenched by the addition of 35 mL of 1 M HCl. The organic layer was separated and washed with brine. The aqueous layer was extracted with EtOAc and the organic layer was dried over $Na_2SO_4$ and filtered. The filtrate was treated with $CH_2N_2/Et_2O$ until TLC analysis revealed the absence of the carboxylic acid. The solvent was evaporated and the residue was dissolved in 100 mL of 1,2-dichloroethane and refluxed with 4 g of $P_2O_5$ for 40 min. The reaction mixture was cooled to room temperature and filtered through a pad of silica gel. The solid was washed thoroughly with EtOAc. The filtrate was evaporated and the residue was dissolved in 100 mL of MeOH and stirred at rt with 4 g of $K_2CO_3$ overnight. The solvent was evaporated and the residue was treated with $H_2O$ and extracted with EtOAc. The organic layer was dried over $Na_2SO_4$ and evaporated to afford 3.4 g of a mixture of (2E)- and (2Z)-3-(4-methanesulfonyl-phenyl)-2-phenyl-but-2-enoic acid methyl ester in about a 1:1 ratio according to $^1$H NMR analysis. The two isomers were separated by flash chromatography to afforded 634 mg of methyl (2E)-3-[4-(methylsulfonyl)phenyl]-2-phenylbut-2-enoate. $^1$H NMR (Acetone-d6, 500 MHz): δ 7.47 (dd, J=6.7, 1.9 Hz, 2 H), 7.36 (dd, J=6.7, 1.9 Hz, 2H), 7.16–7.10 (m, 3 H), 7.06–6.98 (m, 2H), 3.75 (s, 3 H), 3.04 (s, 3H), 2.34 (s, 3H).

Step 2: methyl (2Z)-3-[4-(methylsulfonyl)phenyl]-4-(nitrooxy)-2-phenylbut-2-enoate

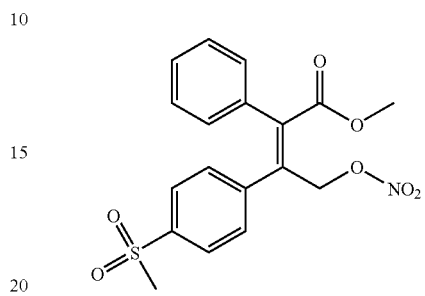

A solution of 600 mg of (E)-3-(4-Methanesulfonyl-phenyl)-2-phenyl-but-2-enoic acid methyl ester (obtained in Step 1) in 40 mL of $CCl_4$ with 2 mmol of NBS and 0.2 mmol of benzoyl peroxide was refluxed for 30 min. Then 0.4 mmol of NBS and 0.1 mmol of benzoyl peroxide were added at the same time and the resulting mixture was refluxed for another 30 min. The mixture was cooled, loaded on a silica gel column, and eluted with 30% EtOAc to afford 750 mg of the desired brominated products as a mixture of (2E)- and (2Z)-isomers about 1:1 ratio according to $^1$H NMR analysis. Without separation, the mixture (750 mg) was dissolved in 40 mL of $CH_3CN$ and treated with 4 mmol of $AgNO_3$ at 50° C. for 15 min. The solvent was evaporated nd the residue was treated with EtOAc and filtered through a pad of silica gel. The residue after evaporation was purified by flash chromatography (15% EtOAc/hexane) over silica gel to afford 161 mg of methyl (2Z)-3-[4-(methylsulfonyl)phenyl] 4-(nitrooxy)-2-phenylbut-2-enoate and 262 mg of methyl (2Z)-3-[4-(methylsulfonyl)phenyl]-4-(nitrooxy)-2-phenyl-but-2-enoate. (2Z)-isomer: MS m/z: 409.1 (M+$NH_4$); $^1$H NMR (Acetone-d6, 500 MHz): δ 7.81 (d, J=8.3 Hz, 2H), 7.49 (d, J=8.3 Hz, 2H), 7.23–7.19 (m, 3 H), 7.14–7.09 (m, 2H), 5.77 (s, 2 H), 3.84 (s, 3H), 3.09 (s, 3H). (2E)-isomer: MS m/z: 409.2 (M+$NH_4$); $^1$H NMR (Acetone-d6, 500 MHz): δ 8.04 (d, J=6.8 Hz, 2H), 7.73 (d, J=6.8 Hz, 2H), 7.61–7.47 (m, 5 H), 5.44 (s, 2 H), 3.48 (s, 3 H), 3.19 (s, 3 H).

Example 2

(2Z)-4-methoxy-2-[4-(methylsulfonyl)phenyl]-4-oxo-3-phenylbut-2-enyl 3-({[tert-butyl(dimethyl)silyl]oxy}methyl)benzoate

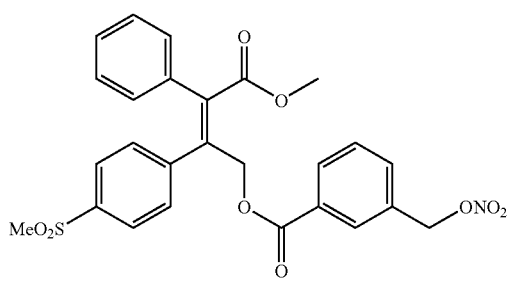

Step 1: (2Z)-4-methoxy-2-[4-(methylsulfonyl)phenyl]-4-oxo-3-phenylbut-2-enyl 3-({[tert-butyl(dimethyl)silyl]oxy}methyl)benzoate

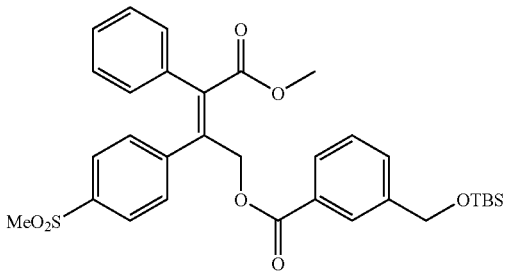

The allylic bromide intermediate from procedure Example 1, step 2 above (410 mg) was dissolved in DMF (10 mL) and treated with Cs$_2$CO$_3$ (575 mg) and 3-({[tert-butyl(dimethyl)silyl]oxy}methyl)benzoic acid (530 mg). The reaction mixture was allowed to stir at room temperature for 2 h. At this time, the reaction mixture was poured into a separatory funnel containing water-ethyl acetate, the layers were separated and the aqueous layer was extracted with ethyl acetate. The combined organic layers were washed with saturated aqueous Na$_2$CO$_3$, water, brine, dried over anhydrous MgSO$_4$ and concentrated. The resulting material was purified by flash chromatography eluting with 20% EtOAc/hexane to yield 260 mg of the title compound as a colorless oil along with 150 mg of the E isomer. (2Z isomer) $^1$H NMR (Acetone-d$_6$, 500 MHz): δ 7.90 (s, 1 H), 7.82 (d, J=8 Hz, 2 H), 7.74 (m, 1 H), 7.60 (m, 1 H), 7.55 (d, J=8 Hz, 21), 7.45 (m, 1 H), 7.18 (m, 3 H), 7.12 (m, 2 H), 5.48 (s, 2 H), 4.80 (s, 2 H), 3.75 (s, 3 H), 3.00 (s, 3H), 0.98 (s, 9H), 0.14 (s, 6H) ppm.

Step 2: (2Z)-4-methoxy-2-[4-(methylsulfonyl)phenyl]-4-oxo-3-phenylbut-2-enyl 3-[(nitrooxy)methyl]benzoate

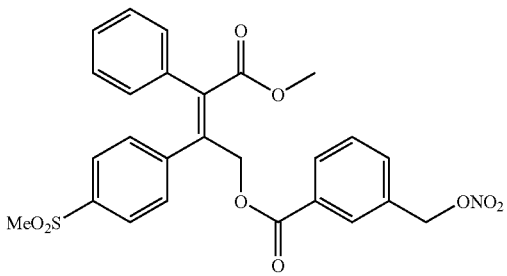

A solution of the above silyl ether (225 mg) in CH$_3$CN (10 mL) was treated with BF-pyridine (0.2 mL) and the reaction mixture was allowed to stir at room temperature for 3 h. During this time an additional 0.2 mL of HF-pyridine reagent was added. The reaction was quenched with 10 mL of a saturated aqueous NaHCO$_3$ solution and the resulting mixture was poured into a separatory funnel containing water/ethyl acetate. The layers were separated and the aqueous layer was extracted with EtOAc (2×), washed with saturated aqueous CuSO$_4$, water, brine, dried over anhydrous MgSO$_4$ and concentrated. The resulting material was filtered through a plug of silica gel eluting with 50% EtOAc/hexane and the corresponding alcohol was isolated as a colourless oil (170 mg). A separate flask was charged with PPh$_3$ (100 mg), CH$_2$Cl$_2$ (10 mL) and at 0° C. was added 0.4 mL of a 1 M Br$_2$ solution in CH$_2$Cl$_2$ and allowed to stir for 10 minutes before the addition of iPr$_2$NEt (75 µL). To this was then added the above alcohol as a CH$_2$Cl$_2$ solution and allowed to stir at 0° C. for 1 h. The reaction mixture was warmed to rt and poured into a separatory funnel containing EtOAc and H$_2$O. The layers were separated and the aqueous layer was extracted with EtOAc. The combined organic layers were washed with H$_2$O, brine, dried over anhydrous MgSO$_4$ and concentrated. This material was further purified by filtering through a plug of silica gel eluting with 40% EtOAc/hexane to provide the corresponding bromide as a faint yellow oil (135 mg). This material was immediately taken up in dry CH$_3$CN (5 mL) and treated with ~85 mg of AgNO$_3$ and heated to 45° C. for 2 h. The reaction mixture was then filtered (to remove AgBr) and concentrated. The resulting material was further purified by flash chromatography eluting with 40% EtOAc/hexane to furnish the nitrate as a colourless oil (115 mg). $^1$H NMR (Acetone-d$_6$, 500 MHz): δ 7.95 (s, 1H), 7.85 (m, 1H), 7.77 (d, J=8.5 Hz, 2H), 7.76 (m, 1H), 7.52 (m, 3H), 7.17 (m, 3H), 7.11 (m, 2H), 5.62 (s, 2H), 5.50 (s, 2H), 3.77 (s, 3H), 3.00 (s, 3H) ppm.

Example 3 methyl (2Z)-3-[4-(methylsulfonyl)phenyl]-4-({[4-(nitrooxy)butoxy]carbonyl}oxy)-2-phenylbut-2-enoate

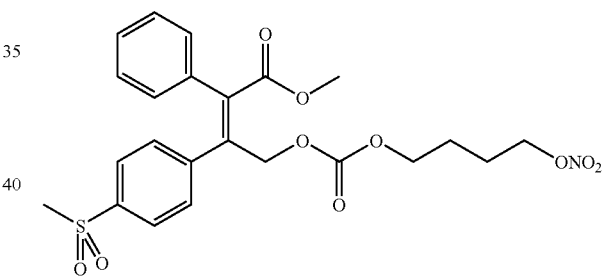

Step 1: (2Z)-2-[4-(methylsulfonyl)phenyl]-3-phenyl-but-2-ene-1,4-diol

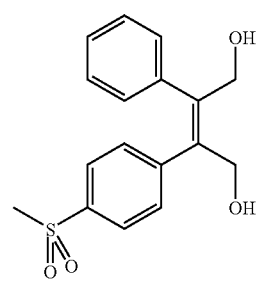

To a solution of 110 g of 4-(4-methanesulfonyl-phenyl)-3-phenyl-5H-furan-2-one in 1.5 L of dichloromethane stirred at −78° C., 150 mL of DIBAL was added dropwise. The resulting mixture was warmed to room temperature and stirred overnight. The reaction mixture was then cooled to −78° C., and 1.2 L of 1 M aqueous NaOH was added dropwise. After the addition, the resulting mixture was warmed to room temperature and the organic phase was separated. The aqueous phase was extracted with dichloromethane. The organic phases were combined and dried over $Na_2SO_4$. 110 g of the titled compound was obtained after evaporation. $^1$H NMR (acetone-d6, 500 M Hz): δ 7.69 (d, 2 H), 7.36 (d, 2 H), 7.16–7.05 (m, 5 H), 4,66 (d, 2 H), 4.63 (d, 2 H), 4.19 (t, 1 H, OH), 4.17 (t, 1 H. OH), 3.04 (s, 3 H).

Step 2: (2Z)-4-{[tert-butyl(dimethyl)silyl]oxy}-2-[4-(methylsulfonyl)phenyl]-3-phenylbut-2-en-1-ol

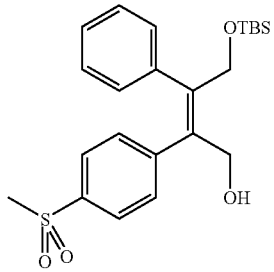

To a solution of 110 g of (2Z)-2-[4-(methylsulfonyl)phenyl]-3-phenylbut-2-ene-1,4-diol and 50 g of imidazole in 1 L of THF stirred at −78° C., a solution 51 g of TBSCl in 250 mL of dichloromethane was added dropwise. The resulting mixture was stirred at −78° C. 0.5 hr. Brine was then added and then warmed to room temperature. The organic phase was separated and the aqueous phase was extracted with EtOAc. The organic phases were combined and dried over $Na_2SO_4$ and evaporated. The resulting crude material was purified by flash chromatography to afford 25.6 g of the title compound as a white solid. $^1$H NMR (acetone-d6, 500 M Hz): δ 7.69 (d, 2 H), 7.37 (d, 2 H), 7.18–7.04 (m, 5 H), 4,77 (s, 2 H), 4.65 (d, 2 H), 3.96 (t, 1H, OH), 3.03 (s, 3 H), 0.84 (s, 9 H), 0.01 (s, 6 H).

Step 3: 4-bromobutyl (2Z)-4-{[tert-butyl(dimethyl)silyl]oxy}-2-[4-(methylsulfonyl)phenyl]-3-phenyl-but-2-enyl carbonate

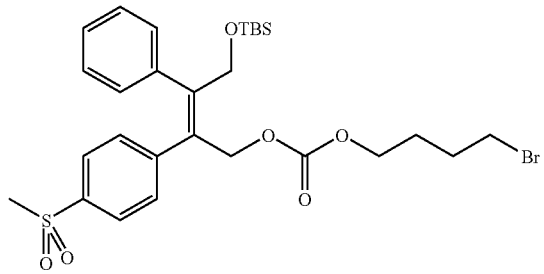

To a solution of phosgene (80 mL, 1.93 M) stirred at −78° C. was added 8 g of 4-bromobutan-1-ol dropwise. The resulting mixture was stirred at rt overnight. The solvent was then removed by distillation. The residue was dissolved in 30 mL of dichloromethane and added to a solution of 5 g of (2Z)-4-{[tert-butyl(dimethyl)silyl]oxy}-2-[4-(methylsulfonyl)phenyl]-3-phenylbut-2-en-1-ol and 15 mL of diisopropylethylamine in 100 mL of dichloromethane stirred at −78° C. The resulting mixture was stirred at rt for 1.5 hr and loaded on a silica gel column and eluted with 5–45% of EtOAc/hexane to afford 5.7 g of the titled compound as a clear oil. $^1$H NMR (acetone-d6, 500 M Hz): δ 7.71 (d, 2 H), 7.37 (d, 2 H), 7.18–7.04 (m, 5 H), 5.30 (s, 2 H), 4.80 (s, 2 H), 4.16 (t, 2 H), 3.53 (t, 2H), 3.06 (s, 3 H), 1.95–1.87 (m, 2 H), 1.82–1.75 (m, 2 H), 0.84 (s, 9 H), 0.02 (s, 6 H).

Step 4: 4-bromobutyl (2Z)-4-hydroxy-2-[4-(methylsulfonyl)phenyl]-3-phenylbut-2-enyl carbonate

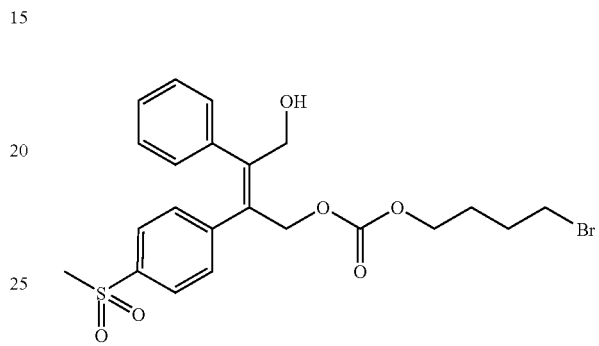

To a solution of 5.7 g of 4-bromobutyl (2Z)-4-hydroxy-2-[4 (methylsulfonyl)phenyl]-3-phenylbut-2-enyl carbonate in 100 mL of MeCN, 5 mL of PyHF was added and the mixture was stirred at rt for 2 hr. The reaction mixture was diluted with 500 mL of toluene and the loaded on a silica gel column and washed with EtOAc. The solvent was evaporated and the residue was purified by flash chromatograph over silica gel to afford 4.3 g of the titled compound. $^1$H NMR (acetone-d6, 500 M Hz): δ 7.69 (d, 2 H), 7.33 (d, 2 H), 7.15–7.00 (m, 5H), 5.30 (s, 2 H), 4.64 (d, 2 H), 4.14 (t, 1 H, OH), 4.12 (t, 2 H), 3.51 (t, 2 H), 3.03 (s, 3 H), 1.91–1.86 (m, 2 H), 1.82–1.76 (m, 2 H).

Step 5: methyl (2Z)-4-{[(4-bromobutoxy)carbonyl]oxy}-3-[4-(methylsulfonyl)phenyl]-2-phenylbut-2-enoate

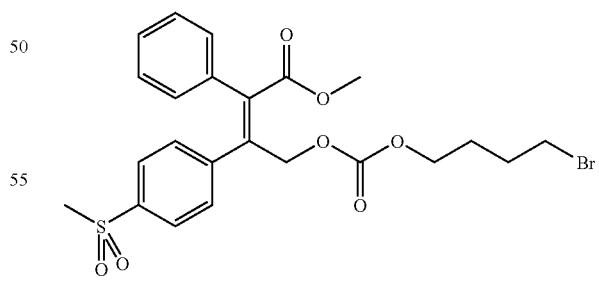

To a solution of 4.2 g of 4-bromobutyl (2Z)-4-hydroxy-2-[4-(methylsulfonyl)phenyl]-3-phenylbut-2-enyl carbonate in 50 mL of dichloromethane, 4.2 g of Dess-Martin reagent was added and the mixture was stirred at rt for 1 hr. Then 0.5 mL of water was added and the mixture was stirred at rt for 0.5 hr. The resulting mixture was filtered and evaporated. The crude thus obtained was dissolved in a solvent mixture of 30 mL of THF with 30 mL of t-BuOH. To this mixture, 5 mL of 2-methyl-2-butene was added followed by the addition of 50 mL of 1 M phosphoric acid and 25 mL of 1 M of $NaClO_2$. The resulting mixture was stirred at rt for 15 min. The organic phase was separated and the aqueous phase was extracted with EtOAc. The organic phase was combined, dried over $Na_2SO_4$, filtered, treated with $CH_2N_2$, and then evaporated. The crude was purified by flash chromatography over silica gel (5–50% EtOAc/hexane) to afford 3.89 g of the titled compound as a clear oil. The solvent was evaporated and the residue was purified by flash chromatograph over silica gel to afford 4.3 g of the titled compound. $^1H$ NMR (acetone-d6, 500 M Hz): δ 7.80 (d, 2 H), 7.47 (d, 2 H), 7.22–7.15 (m, 3 H), 7.12–7.05 (m, 2 H), 5.30 (s, 2 H), 4.14 (t, 2 H), 3.82 (s, 3 H), 3.53 (t, 2 H), 3.09 (s, 3 H), 1.91–1.86 (m, 2H), 1.81–1.70 (m, 2H).

Step 6: methyl (2Z)-3-[4-(methylsulfonyl)phenyl]-4-({[4-(nitrooxy)butoxy]carbonyl}oxy)-2-phenylbut-2-enoate

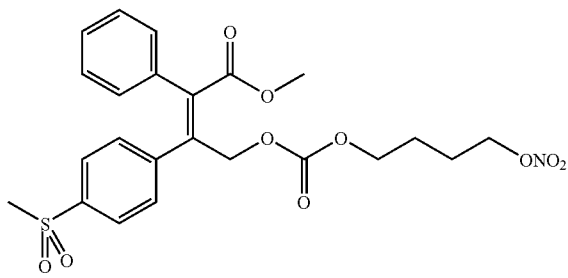

A solution of 3.89 g of methyl (2Z)-4-{[(4-bromobutoxy)carbonyl]oxy}-3-[4-(methylsulfonyl)phenyl]-2-phenylbut-2-enoate and 4 g of $AgNO_3$ in 80 mL of MeCN was heated to 85° C. for 1.5 hr. The solvent was evaporated and the residue was stirred with EtOAc for 10 min and filtered. The solvent was evaporated and the residue was purified by flash chromatography over silica gel (5–45% EtOAc/hexane) to afford 3.5 g of the titled compound as a white solid. $^1H$ NMR (acetone-d6, 500 M Hz): δ 7.80 (d, 2 H), 7.47 (d, 2 H), 7.22–7.15 (m, 3 H), 7.12–7.05 (m, 2 H), 5.30 (s, 2 H), 4.58 (t, 2 H), 4.15 (t, 2 H), 3.82 (s, 3 H), 3.09 (s, 3 H), 1.82–1.69 (m, 4 H).

Example 4

(2Z)-3-[4-(methylsulfonyl)phenyl]-4-{[6-(nitrooxy)hexanoyl]oxy}-2-phenylbut-2-enoic acid

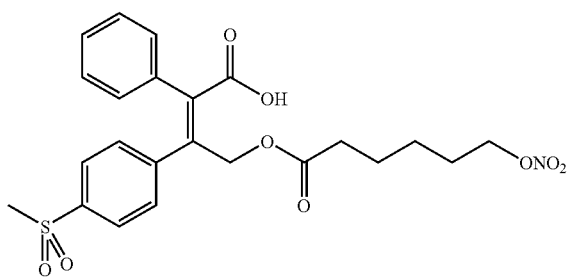

Step 1: (2Z)-2-[4-(methylsulfonyl)phenyl]4-oxo-3-phenylbut-2-enyl 6-(nitrooxy)hexanoate

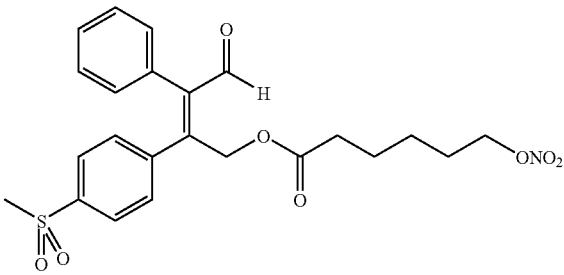

To a solution of 6 g of (2Z)-4-{[tert-butyl(dimethyl)silyl]oxy}-2-[4-(methylsulfonyl)phenyl]-3-phenylbut-2-en-1-ol, from Step 2, Example 3, 2.8 mL of diisopropylethylamine, and 1.8 g DMAP in 150 mL of dichloromethane stirred at −78° C., 15 mmol of 6-bromohexanoyl chloride was added The resulted mixture was stirred at rt for 1.5 hr and loaded on a silica gel column and eluted with 30–50% of EtOAc/hexane to afford a clear oil, which was dissolved 80 ml of MeCN with 7 g of $AgNO_3$ in 80 mL of MeCN and heated to 85° C. for 1.5 hr. The solvent was evaporated and the residue was stirred with EtOAc for 10 min and filtered. The filtrate was evaporated and the residue was dissolved in 80 mL of MeCN. To the resulting solution, 4 mL of PyHF was added and the mixture was stirred at rt for 1.5 hr. The reaction mixture was diluted with 400 mL of toluene and then loaded on silica gel column and washed with EtOAc. The solvent was evaporated and the residue was dissolved in 80 mL of dichloromethane and 7 g of Dess-Martin reagent was thus added. The resulted mixture was stirred at rt for 1 hr and treated with 0.5 mL of water for 10 hr. The resulting mixture was filtered and evaporated, and the residue was purified by flash chromatography to afford 4.3 g of the title compound as a clear oil. $^1H$ NMR (acetone-d6, 500 M Hz): δ 10.51 (s, 1 H), 7.80 (d, 2 H), 7.47 (d, 2 H), 7.22–7.15 (m, 3 H), 7.04–6.97 (m, 2 H), 5.67 (s, 2 H), 4.52 (t, 2 H), 3.08 (s, 3 H), 2.27 (t, 2 H), 1.72–1.69 (m, 2 H), 1.55–1.48 (m, 2 H), 1.38–1.29 (m, 2 H).

Step 2: (2Z)-3-[4-(methylsulfonyl)phenyl]-4-{[6-(nitrooxy)hexanoyl]oxy}-2-phenylbut-2-enoic acid

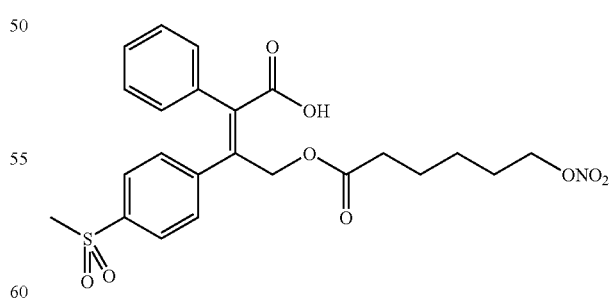

To a solution of 4.3 g of (2Z)-2-[4-(methylsulfonyl)phenyl]-4-oxo-3-phenylbut-2-enyl 6-(nitrooxy)hexanoate in a solvent mixture of 50 mL of THF with 50 mL of t-BuOH, 5 mL of 2-methyl-2-butene was added followed by the addition of 20 mL of 2 M phosphoric acid and 20 mL of 1 M of $NaClO_2$. The resulting mixture was stirred at rt for 15 min. The organic phases were separated and the aqueous phase was extracted with EtOAc. The organic phases were combined, dried over Na₂SO₄, filtered, and then evaporated. The crude was purified by flash chromatography over silica gel (5–100% EtOAc/hexane) to afford 3.8 g of the titled compound as white solid. $^1$H NMR (acetone-d6, 500 M Hz): δ 7.79 (d, 2H), 7.45 (d, 2 H), 7.22–7.15 (m, 3 H), 7.15–7.10 (m, 2 H), 5.31 (s, 2 H), 4.51 (t, 2 H), 3.07 (s, 3 H), 2.23 (t, 2 H), 1.72–1.65 (m, 2 H), 1.52–1.45 (m, 2 H), 1.37–1.29 (m, 2 H).

Example 5 methyl (2Z)-3-[4-(methylsulfonyl)phenyl]-4-{[6-(nitrooxy)hexanoyl]oxy}-2-phenylbut-2-enoate

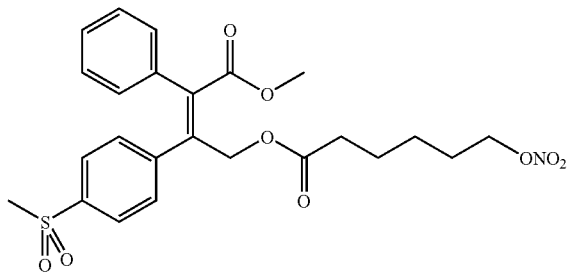

To a solution of 30 mg of (2Z)-3-[4-(methylsulfonyl)phenyl]-4-{[6-(nitrooxy)hexanoyl]oxy}-2-phenylbut-2-enoic acid (prepared as described in Step 2 of EXAMPLE 4) in 5 mL of THE, CH₂N₂/Et₂O was added dropwise. The excess CH₂N₂ was removed by the addition of a dilute acetic acid ether solution. The solvent was evaporated to afford 31 mg of the title compound as a clear oil. $^1$H NMR (acetone-d6, 500 M Hz δ 7.79 (d, 2 H), 7.46 (d, 2 H), 7.22–7.17 (m, 3 H), 7.14–7.08 (m, 2 H), 5.24 (s, 2 H), 4.52 (t, 2 H), 3.82 (s, 3 H), 3.08 (s, 3 H), 2.25 (t, 2 H), 1.73–1.66 (m, 2 H), 1.56–1.48 (m, 2 H), 1.39–1.31 (m, 2 H).

Example 6 ethyl (2Z)-3-[4-(methylsulfonyl)phenyl]-4-({[4-(nitrooxy)butoxy]carbonyl}oxy)-2-phenylbut-2-enoate

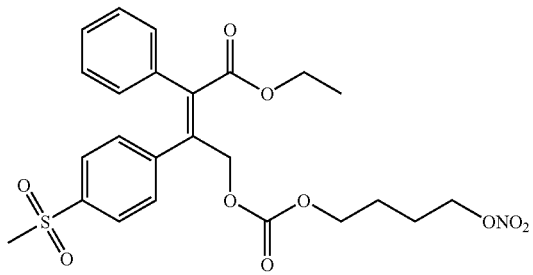

Step 1: 4-bromobutyl (2Z)-4-{[tert-butyl(dimethyl)silyl]oxy}-2-[4-(methylsulfonyl)phenyl]-3-phenyl-but-2-en-1-yl carbonate

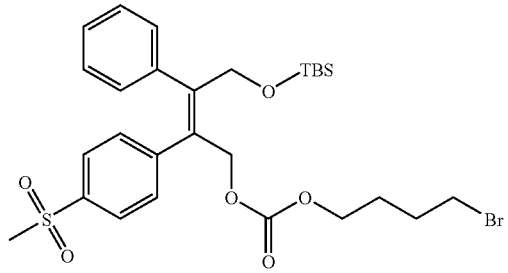

To a solution of 80 mL of phosgene/toluene (1.93 M) stirred at −78° C., 8 g of 4-bromo-1-butanol was added. The resulting mixture was stirred at rt overnight and distilled to remove toluene. The residue was dissolved in 30 mL of dichloromethane and added to a mixture formed by 15 mL of Hunig's base, 10 mmol of (2Z)-4-{[tert-butyl(dimethyl)silyl]oxy}-2-[4-(methylsulfonyl)phenyl]-3-phenylbut-2-en-1-ol, and 100 mL of dichloromethane stirred −78° C. The reaction mixture was stirred at rt for 1.5 h, filtered through a pad of silica gel, washed with EtOAc, evaporated, and purified by flash chromatography (5–50% EtOAc/hexane) to afford 5.7 g of the titled compound. $^1$H NMR (acetone-d6, 500 MHz): δ 7.72 (d, 2 H), 7.38 (d, 2 H), 7.18–7.05 (m, 5 H), 5.30 (s, 2 H), 4.81 (s, 2 H), 4.15 (t, 2 H), 3.53 (t, 2 H), 3.07 (s, 3 H), 1.96–1.87 (m, 2 H), 1.83–1.75 (m, 2 H), 0.82 (s, 9 H), 0.00 (s, 6 H).

Step 2: 4-bromobutyl (2Z)-4-hydroxy-2-[4-(methylsulfonyl)phenyl]-3-phenylbut-2-en-1-yl carbonate

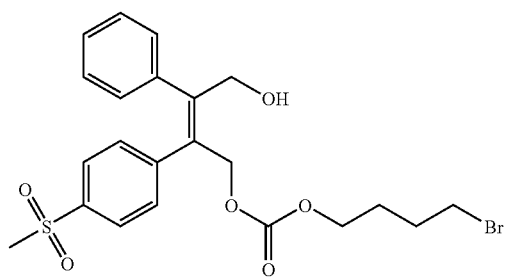

A mixture of 5.7 g of 4-bromobutyl (2Z)-4-{[tert-butyl(dimethyl)silyl]oxy}-2-[4-(methylsulfonyl)phenyl]-3-phenylbut-2-en-1-yl carbonate and 5 mL of PyHF in 100 mL of MeCN was stirred at rt for 2 h, diluted with 500 mL of toluene, filtered through a pad of silica gel, evaporated, and purified by flash chromatography to afford 4.3 g of the titled compound. $^1$H NMR (acetone-d6, 500 MHz): δ 7.70 (d, 2 H), 7.36 (d, 2 H), 7.18–7.10 (m, 5 H), 5.30 (s, 2 H), 4.68 (d, 2 H), 4.15 (t, 1 H, OH), 4.13 (t, 2 H), 3.53 (t, 2 H), 3.07 (s, 3 H), 1.93–1.87 (m, 2 H), 1.80–1.70 (m, 2 H).

Step 3: (2Z)-4-{[(4-bromobutoxy)carbonyl]oxy}-3-[4-(methylsulfonyl)phenyl]-2-phenylbut-2-enoic acid

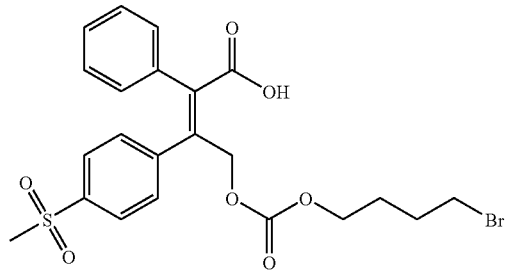

A solution of 4.2 g of 4-bromobutyl (2Z)-4-hydroxy-2-[4-(methylsulfonyl)phenyl]-3-phenylbut-2-en-1-yl carbonate in 50 mL of dichloromethane was treated with 4.2 g of Dess-Martin reagent for 1 h at rt. The reaction was quenched by 0.5 mL of water and stirred at rt for 1 h, filtered, and evaporated. The residue was dissolved in a solvent mixture of 30 mL of THF and 30 mL of t-BuOH, and treated with 50 mL of 1 M of $H_3PO_4$ and 25 mL of 1 M of $NaClO_2$ in the presence of 5 mL of 2-methyl-2-butene. The resulting mixture was stirred at rt for 15 min; the organic layer was separated, washed with brine, dried ($Na_2SO_4$), and evaporated to afford 4 g of the crude acid for further use.

Step 4: ethyl (2Z)-4-{[(4-bromobutoxy)carbonyl]oxy}-3-[4-(methylsulfonyl)phenyl]-2-phenylbut-2-enoate

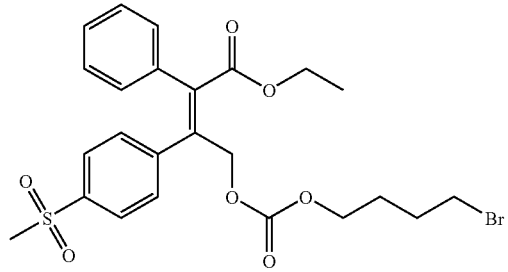

A solution of 5 mmol of (2Z)-4-{[(4-bromobutoxy)carbonyl]oxy}-3-[4-(methylsulfonyl)phenyl]-2-phenylbut-2-enoic acid with 3 mL of EtI in 30 mL of DMF was stirred with 5 mmol of $K_2CO_3$ at rt for 30 min. The reaction was quenched with sat. $NH_4Cl/H_2O$, extracted with EtOAc, Dried over $Na_2SO_4$, evaporated, and purified by flash chromatography (5–50% EtOAc/hexane) to afford 2.7 g of the titled compound. $^1$H NMR (acetone-d6, 500 MHz): δ 7.80 (d, 2 H), 7.48 (d, 2 H), 7.22–7.17 (m, 3 H), 7.15–7.08 (m, 2 H), 5.30 (s, 2 H), 4.32 (m, 4 H), 3.54 (t, 2 H), 3.12 (s, 3 H), 1.95–1.84 (m, 2 H), 1.83–1.70 (m, 2 H) 1.31 (t, 3 H).

Step 5: ethyl (2Z)-3-[4-(methylsulfonyl)phenyl]-4-({[4-(nitrooxy)butoxy]carbonyl}oxy)-2-phenylbut-2-enoate

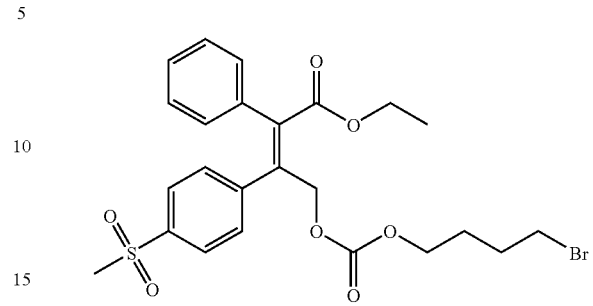

A solution of 2.7 g of ethyl (2Z)-4-{[(4-bromobutoxy)carbonyl]oxy}-3-[4-(methylsulfonyl)phenyl]-2-phenylbut-2-enoate and 2.7 g of $AgNO_3$ in 30 mL of acetonitrile was heated to 85° C. for 0.5 h. The solvent was evaporated and the residue was stirred with EtOAc for 10 min, filtered, evaporated, and purified by flash chromatography over silica gel (5–55% EtOAc/hexane) to afford 2.18 g of the titled compound as a clear oil. $^1$H NMR (acetone-d6, 500 MHz): δ 7.82 (d, 2 H), 7.47 (d, 2 H), 7.23–7.17 (m, 3 H), 7.14–7.07 (m, 2 H), 5.30 (s, 2 H), 4.58 (t, 2 H), 4.32 (q, 2 H), 4.16 (t, 2 H), 3.10 (s, 3 H), 1.82–1.71 (m, 4 H), 1.30 (t, 3 H).

Example 7

(2Z)-3-[4-(methylsulfonyl)phenyl]-4-[({[6-(nitrooxy)hexyl]oxy}carbonyl)oxy]-2-phenylbut-2-enoic acid

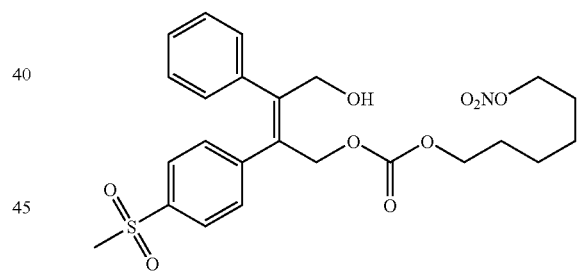

Strp 1: 6-bromohexyl (2Z)-4{[tert-butyl(dimethyl)silyl]oxy}-2-[4-(methylsulfonyl)phenyl]-3-phenylbut-2-en-1-yl carbonate

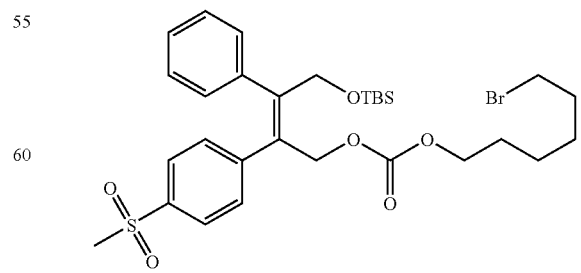

To a solution of 90 ml of phosgene (1.93 M/toluene) at −78° C. under $N_2$, was added 12.6 g of 6-bromohexanol. The resulting mixture was stirred at 25° C. for 24 h. Distillation of excess phosgene was done under low vacuum at 150° C. to afford 16.9 g of the desired compound as orange oil. The crude thus obtained was dissolved in dichloromethane, and added to a solution of 16.3 g of (2Z)-4-{[tert-butyl(dimethyl)silyl]oxy}-2-[4-(methylsulfonyl)phenyl]-3-phenylbut-2-en-1-ol, 4.6 g of DMAP and 8.5 mL of Hünig's base in 250 mL of CH$_2$Cl$_2$ at –78° C. The reaction mixture was stirred for 1 h at 25° C. and then filtered through a pad of silica gel, washed with EtOAc, evaporated, and purified by flash chromatography to afford 24.1 g of the titled compound as yellowish oil.

Step 2: 6-bromohexyl (2Z)-4-hydroxy-2-[4-(methylsulfonyl)phenyl]-3-phenylbut-2-en-1-yl carbonate

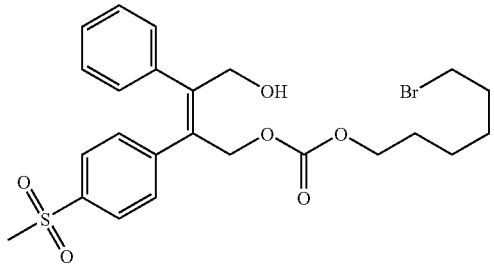

To a solution of 24 g of 6-bromohexyl (2Z)-4-{[tert-butyl (dimethyl)silyl]oxy}-2-[4-(methylsulfonyl)phenyl]-3-phenylbut-2-en-1-yl carbonate in 200 mL of acetonitrile was added 9 mL of PyrHF and the mixture was stirred at 25° C. for 1.5 h. The reaction mixture was diluted with 1 L of toluene, loaded on silica gel and washed with EtOAc. The solvent was evaporated to afford 16.8 g of the titled compound. The crude compound was used directly for the next step.

Step 3: (2Z)-4-hydroxy-2-[4-(methylsulfonyl)phenyl]-3-phenylbut-2-en-1-yl 6-(nitrooxy)hexyl carbonate

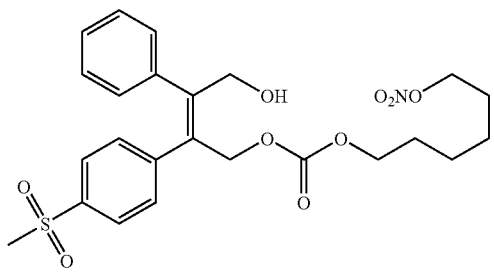

A solution of 4.7 g of 6-bromohexyl (2Z)-4-hydroxy-2-[4-(methylsulfonyl)phenyl]-3-phenylbut-2-en-1-yl carbonate and 7.7 g of AgNO$_3$ in 40 mL of acetonitrile was heated to 85° C. for 100 min. The solvent was evaporated. The residue was stirred with EtOAc for 10 min, filtered, evaporated, and purified by flash chromatography over silica gel (5–55% EtOAc/hexane) to afford 4.6 g of the titled compound as a yellowish oil. $^1$H NMR (acetone-d6, 500 MHz): □ 7.76 (d, 2 H), 7.43 (d, 2 H), 7.18–7.04 (m, 5 H), 5.18 (s, 2 H), 4.75 (s, 2 H), 4.50 (t, 2 H), 4.24 (t, 2 H), 3.05 (s, 3 H) 1.75–1.65 (m, 4 H), 1.44–1.31 (m, 4 H).

Step 4: (2Z)-3-[4-(methylsulfonyl)phenyl]-4-[({[6-(nitrooxy)hexyl]oxy}carbonyl)oxy]-2-phenylbut-2-enoic acid

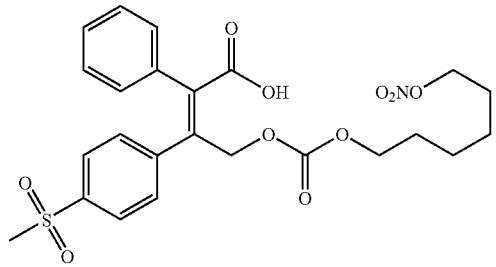

A solution of 4.5 g of (2Z)-4-hydroxy-2-[4-(methylsulfonyl)phenyl]-3-phenylbut-2-en-1-yl 6-(nitrooxy)hexyl carbonate in 100 mL of dichloromethane was treated with 4.5 g of Dess-Martin reagent at 25° C. for 75 min. The reaction was quenched by 1 mL of water, and stirred at RT for 30 min. Then the mixture was filtered through a pad of silica gel and evaporated. The crude thus obtained was dissolved in a solvent mixture of THF and t-BuOH (100 mL/100 mL). To the resulting solution was added 5.3 mL of 2-methyl-2-butene followed by the addition of 13 mL of phosphoric acid (1.2 M soln) and 13 mL of NaClO$_2$ (1M soln). The resulting mixture was stirred at RT for 30 min. The organic phase was separated and the aqueous phase was extracted with EtOAc. The organic phases were combined, dried over Na$_2$SO$_4$, filtered, and then evaporated. The crude was purified by flash chromatography to afford titled compound as a white solid. $^1$H NMR (acetone-d6, 500 MHz): δ 11.8 (bs, 1 H), 7.76 (d, 2 H), 7.43 (d, 2 H), 7.17–7.11 (m, 5 H), 5.34 (s, 2 H), 4.52 (t, 2 H), 4.04 (t, 2 H), 3.05 (s, 3 H), 1.71 (m, 2 H), 1.57 (m, 2 H), 1.40 (m, 2 H), 1.34 (m, 2 H).

Example 8

Methyl (2Z)-3-[4-(methylsulfonyl)phenyl]-4-[({[6-(nitrooxy)hexyl]oxy}carbonyl)oxy]-2-phenylbut-2-enoate

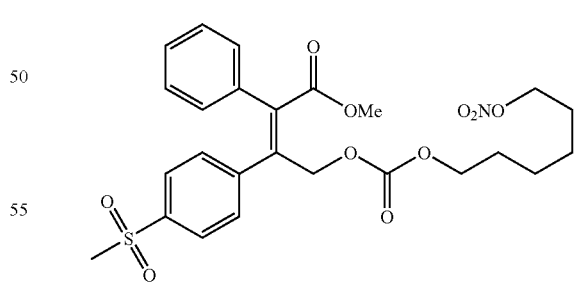

By treatment of a THF solution of (2Z)-3-[4-(methylsulfonyl)phenyl]4-[({[6-(nitrooxy)hexyl]oxy}carbonyl)oxy]-2-phenylbut-2-enoic acid with diazomethane, the titled compound was obtained (1 g) as a white solid. $^1$H NMR (acetone-d6, 500 MHz): δ 7.77 (d, 2 H), 7.44 (d, 2 H), 7.17–7.15 (m, 3 H), 7.09–7.06 (m, 2 H), 5.26 (s, 2 H), 4.53 (t, 2 H), 4.06 (t, 2 H), 3.79 (s, 3 H), 3.05 (s, 3 H), 1.75–1.69 (m, 2 H), 1.63–1.57 (m, 2 H), 1.45–1.33 (m, 4 H).

Example 9

Ethyl (2Z)-3-[4-(methylsulfonyl)phenyl]-4-[({[6-(nitrooxy)hexyl]oxy}carbonyl)oxy]-2-phenylbut-2-enoate

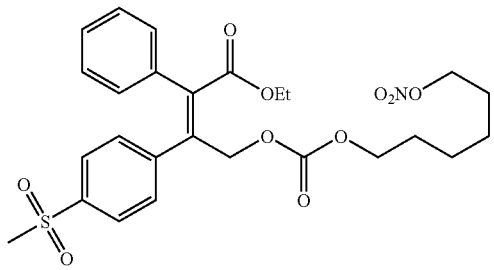

Step 1: (2Z)-4-({[(6-bromohexyl)oxy]carbonyl}oxy)-3-[4-(methylsulfonyl)phenyl]-2-phenylbut-2-enoic acid

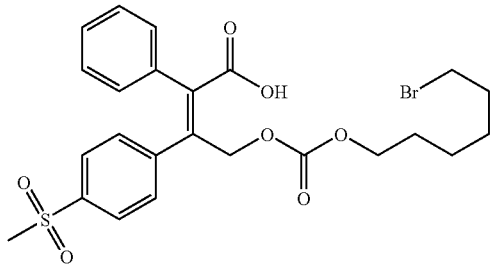

To a solution of 12 g of 6-bromohexyl (2Z)-4-hydroxy-2-[4-(methylsulfonyl)phenyl]-3-phenylbut-2-en-1-yl carbonate in 125 mL of dichloromethane was added 12.1 g of Dess-Martin reagent; the resulting mixture was stirred at 25° C. for 2 h. Then 1 mL of water was added and the mixture was stirred at RT for 30 min. The mixture was filtered through a pad of silica gel and evaporated. The crude thus obtained was dissolved in a solvent mixture of THF and t-BuOH (100 mL/100 mL). To this solution was added 16 mL of 2-methyl-2-butene followed by the addition of 40 mL of phosphoric acid (1.2M soln) and 40 mL of NaClO₂ (1M soln). The resulting mixture was stirred at RT for 30 min. The organic phase was separated and the aqueous phase was extracted with EtOAc. The organic phases were combined, dried over Na₂SO₄, filtered, and then evaporated. The crude was purified by flash chromatography to afford titled compound as white solid.

Step 2: ethyl (2Z)-4-({[(6-bromohexyl)oxy]carbonyl}oxy)-3-[4-(methylsulfonyl)phenyl]-2-phenylbut-2-enoate

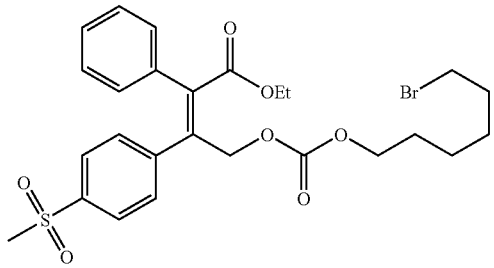

To a solution of 2.6 g of (2Z)-4-({[(6-bromohexyl)oxy]carbonyl}oxy)-3-[4-(methylsulfonyl)phenyl]-2-phenylbut-2-enoic acid in 20 mL of DMF at rt was added 3.8 mL of ethyl iodide and 670 mg of potassium carbonate under nitrogen. The reaction was stirred for 1 h, quenched by saturated aqueous NH₄Cl, extracted with EtOAc, washed with water (3×), brine, and dried over sodium sulfate. Purification by flash chromatography afforded 1.86 g of the titled compound as a brownish oil.

Step 3: Ethyl (2Z)-3-[4-(methylsulfonyl)phenyl]-4-[({[6-(nitrooxy)hexyl]oxy}carbonyl)oxy]-2-phenylbut-2-enoate

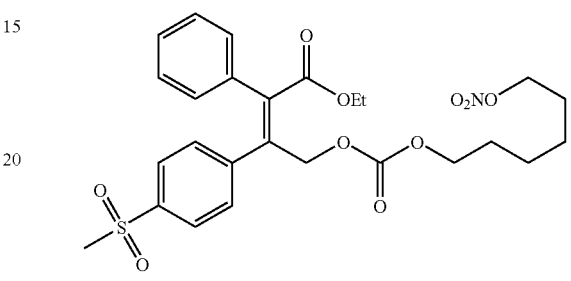

A solution of 1.86 g of ethyl (2Z)-4-({[(6-bromohexyl)oxy]carbonyl}oxy)-3-[4-(methylsulfonyl)phenyl]-2-phenylbut-2-enoate and 2.8 g of AgNO₃ in 30 μL of acetonitrile was heated to 85° C. for 1 h. The solvent was evaporated and the residue was stirred with EtOAc for 10 min, filtered, and evaporated. The compound was then purified by flash chromatography over silica gel (5–55% EtOAc/hexane) to afford 1.0 g of the titled compound as a colorless oil. $^1$H NMR (acetone-d6, 500 MHz): δ 7.77 (d, 2 H), 7.47–7.44 (d, 2 H), 7.18–7.16 (m, 3 H), 7.10–7.07 (m, 2 H), 5.25 (s, 2 H), 4.53 (t, 2 H), 4.28 (q, 2 H), 4.07 (t, 2 H), 3.06 (s, 3 H), 1.75–1.69 (m, 2 H), 1.63–1.57 (m, 2 H), 1.45–1.33 (m, 4 H), 1.27 (t, 3 H).

Example 10

2-(diethylamino)ethyl (2Z)-3-[4-(methylsulfonyl)phenyl]-4-{[6-(nitrooxy)hexanoyl]oxy}-2-phenylbut-2-enoate

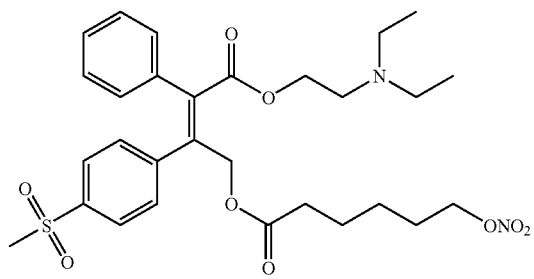

To a solution of 1.5 g of (2Z)-3-[4-(methylsulfonyl)phenyl]-4-{[6-(nitrooxy)hexanoyl]oxy}-2-phenylbut-2-enoic and 0.8 g of 2-bromo-N,N-diethylethylamine hydrobromide in 15 mL of DMF was stirred at rt with 0.8 g K₂CO₃ for 2 hr. Then saturated ammonium chloride solution was added and the mixture was extracted with EtOAc. The organic layer was combined and washed with brine and dried over Na₂SO₄. The solvent was evaporated and the residue was purified by flash chromatography over silica gel (5–50% EtOAc/hexane) to afford 1.2 g of the titled compound as an oil. $^1$H NMR (500 MHz, Acetone-d6): δ 7.78 (d, 2 H), 7.45 (d, 2 H), 7.24–7.15 (m, 5 H), 5.40 (s, 2 H), 4.78 (t, 2 H), 4.52 (t, 2 H), 3.42 (m, 2 H), 3.10–3.00 (m, 7 H), 2.25 (t, 2 H), 1.68 (m, 2 H), 1.50 (m, 2 H), 1.33 (m, 2 H), 1.24 (t, 6 H).

Example 11

(1S)-2-tert-butoxy-1-methyl-2-oxoethyl (2Z)-3-[4-(methylsulfonyl)phenyl]-4-{[6-(nitrooxy)hexanoyl]oxy}-2-phenylbut-2-enoate

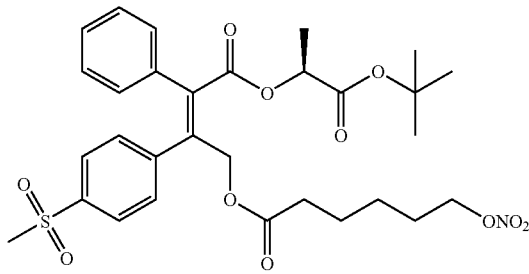

To a solution of 0.3 g (2Z)-3-[4-(methylsulfonyl)phenyl]-4-{[6-(nitrooxy)hexanoyl]oxy}-2-phenylbut-2-enoic from step 5 example 1 and 0.12 g of DMAP and 0.08 g of tert-butyl(2R)-2-hydroxypropionate in 5 mL of CH$_2$Cl$_2$ at 0° C. was added 0.1 g of EDCl. The reaction mixture was stirred overnight. Then saturated ammonium chloride solution was added and the mixture was extracted with EtOAc. The organic layer was combined, washed with brine and dried over Na$_2$SO$_4$. The solvent was evaporated and the residue was purified by flash chromatography over silica gel (5% EtOAc/hexane) to afford (1S)-2-tert-butoxy-1-methyl-2-oxoethyl (2Z)-3-[4-(methylsulfonyl)phenyl]-4-{[6-(nitrooxy)hexanoyl]oxy}-2-phenylbut-2-enoate. $^1$H NMR (500 MHz, Acetone-d6): δ 7.80 (d, 2 H), 7.48 (d, 2 H), 7.17–7.09 (m, 5 H), 5.34 (s, 2 H), 5.10 (m, 1 H), 4.50 (t, 2 H), 3.08 (s, 3 H), 2.22 (t, 2 H), 1.69 (m, 2 H), 1.48 (m, 14 H), 1.32 (m, 2 H).

Example 12

(2S)-2-[((2Z)-3-[4-(methylsulfonyl)phenyl]-4-{[6-(nitrooxy)hexanoyl]oxy}-2-phenylbut-2-enoyl)oxy]propanoic acid

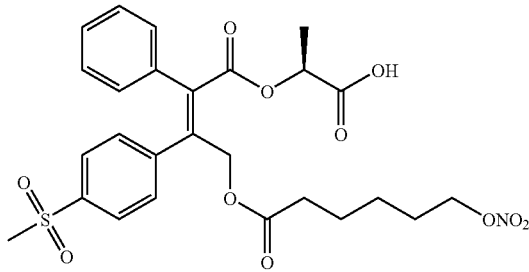

The titled compound (0.25 g) was obtained as a white powder after a TFA treatment of the (1S)-2-tert-butoxy-1-methyl-2-oxoethyl (2Z)-3-[4-(methylsulfonyl)phenyl]-4-{[6-(nitrooxy)hexanoyl]oxy}-2-phenylbut-2-enoate as prepared above. $^1$H NMR (500 MHz, Acetone-d6): δ 7.80 (d, 2 H), 7.48 (d, 2 H), 7.17–7.09 (m, 5 H), 5.34 (s, 2 H), 5.25 (m, 1 H), 4.50 (t, 2 H), 3.08 (s, 3 H), 2.25 (t, 2 H), 1.69 (m, 2 H), 1.55 (d, 3 H), 1.49 (m, 2 H), 1.32 (m, 2 H).

Example 13 methyl (2Z)-3-[4-(methylsulfonyl)phenyl]-4-[({[5-(nitrooxy)pentyl]oxy}carbonyl)oxy]-2-phenylbut-2-enoate

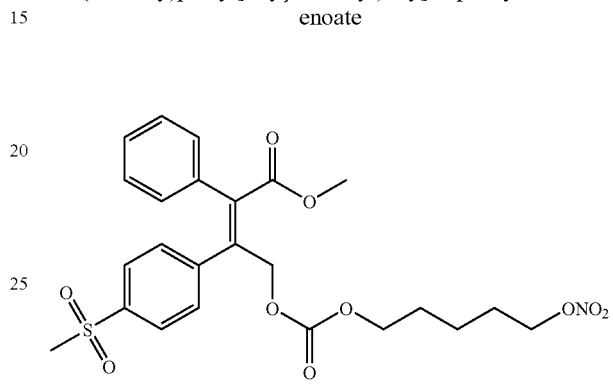

Step 1: 5-bromopentyl (2Z)-4-{[tert-butyl(dimethyl)silyl]oxy}-2-[4-(methylsulfonyl)phenyl]-3-phenyl-but-2-enyl carbonate

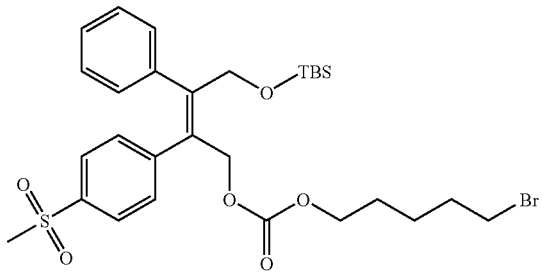

To a solution of 5-bromo-1-pentanol (1 eq, 0.35M) in CH$_2$Cl$_2$ was added pyridine (1.1 eq). The mixture was cooled at −78° C. and a solution of triphosgene (0.33 eq, 0.1M) was slowly added, the mixture was warmed to rt and stirred for 5 min. The reaction mixture was then slowly added to a mixture of (2Z)-4-{[tert-butyl(dimethyl)silyl]oxy}-2-[4-(methylsulfonyl)phenyl]-3-phenylbut-2-en-1-ol (L eq) and pyridine (1 eq) in CH$_2$Cl (0.35M) precooled at −78° C. The reaction mixture was warmed to 0° C. and stirred 5 min. Saturated aqueous ammonium chloride was added and the mixture was extracted with EtOAc. The combined organic layers were dried over Na$_2$SO$_4$, filtered and concentrated. The residue was purified by flash chromatography on silica gel eluted with 1:6 to 1:1 EtOAc/hexanes to give the titled compound.

Step 2: 5-bromopentyl (2Z)-4-hydroxy-2-[4-(methylsulfonyl)phenyl]-3-phenylbut-2-enyl carbonate

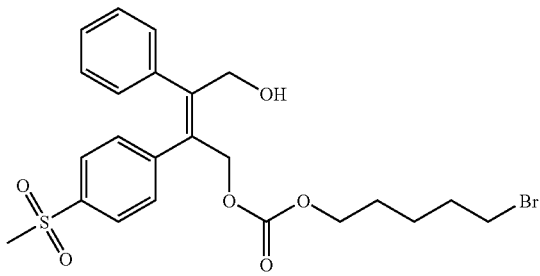

A mixture of 5-bromopentyl (2Z)-4-{[tert-butyl(dimethyl)silyl]oxy}-2-[4-(methylsulfonyl)phenyl]-3-phenylbut-2-enyl carbonate (1 eq) and PyrHF (excess) in MeCN (0.25 M) was stirred at rt for 2 h, diluted with 5 volumes of toluene, filtered through a pad of silica gel eluted with 70% EtOAc/hexanes to give the titled compound.

Step 3: (2Z)-4-hydroxy-2-[4-(methylsulfonyl)phenyl]-3-phenylbut-2-enyl 5-(nitrooxy)pentyl carbonate

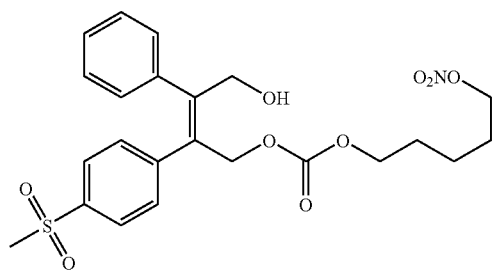

To a solution of 5-bromopentyl (2Z)-4-hydroxy-2-[4-(methylsulfonyl)phenyl]-3-phenylbut-2-enyl carbonate (1 eq, 0.11M) in AcCN was added AgNO$_3$ (10 eq) and the mixture was heated to 85° C. for 0.5 h. The solvent was evaporated and the residue was stirred with EtOAc for 10 min, filtered on a silica gel pad eluted with 70% EtOAc/hexane to afford titled compound.

Step 4: (2Z)-3-[4-(methylsulfonyl)phenyl]-4-[({[5-(nitrooxy)pentyl]oxy}carbonyl)oxy]-2-phenylbut-2-enoic acid

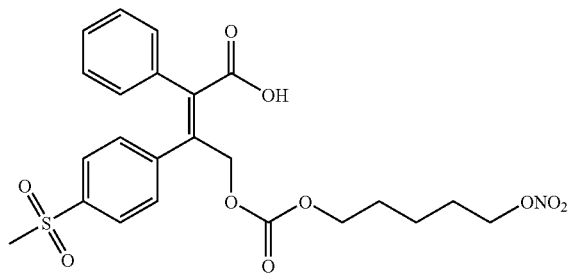

A solution of (2Z)-4-hydroxy-2-[4-(methylsulfonyl)phenyl]-3-phenylbut-2-enyl 5-(nitrooxy)pentyl carbonate (1 eq, 0.2M) in dichloromethane was treated with Dess-Martin reagent (1.3 eq) for 1 h at rt. The reaction was quenched by 10 eq of water and stirred at rt for 1 h, filtered on a silica gel pad eluted with 60% EtOAc/hexanes and evaporated. The residue was dissolved in a 3:1 solvent mixture of tBuOH/CH$_2$Cl$_2$, and treated with 1 M H$_3$PO$_4$ (4 eq) and 1 M NaClO$_2$ (2 eq) in the presence of an excess of 2-methyl-2-butene. The resulting mixture was stirred at rt for 30 min, diluted with EtOAc and the organic layer was separated, washed with brine, dried (Na$_2$SO$_4$), and evaporated to afford the crude acid used as such for next step.

Step 5: methyl (2Z)-3-[4-(methylsulfonyl)phenyl]-4-[({[5-(nitrooxy)pentyl]oxy}carbonyl)oxy]-2-phenylbut-2-enoate

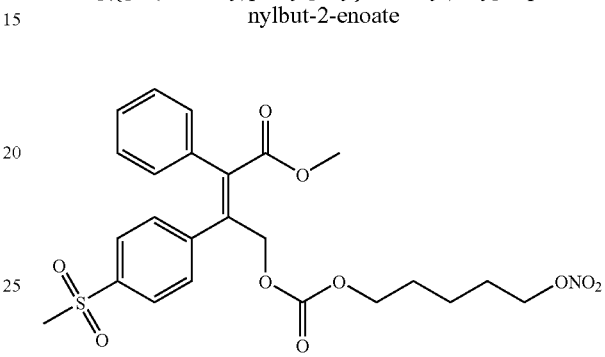

Diazomethane (excess) was added to the previous acid in THF. The reaction mixture was concentrated and the residue was purified by flash chromatography on silica gel eluted with 15%–40% EtOAc/hexane to afford the corresponding methyl ester. MS (+APCI) m/z 539.2 (M+H2O)+

Example 14

N,N-diethyl-2-({(2Z)-3-[4-(methylsulfonyl)phenyl]-4-[({[5-(nitrooxy)pentyl]oxy}carbonyl)oxy]-2-phenylbut-2-enoyl}oxy)ethanaminium chloride

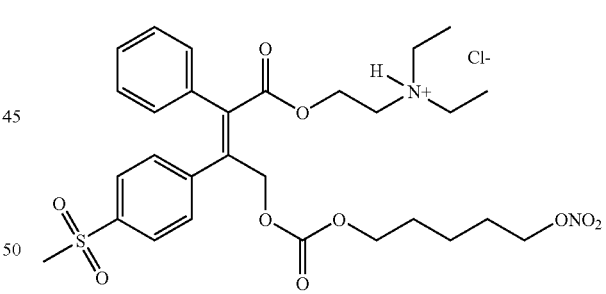

To a solution of (2Z)-3-[4-(methylsulfonyl)phenyl]-4-[({[5-(nitrooxy)pentyl]oxy}carbonyl)oxy]-2-phenylbut-2-enoic acid (1 eq, 0.2M) in DMF was added 2-bromo-N,N-diethylethanaminium bromide (1 eq) and K$_2$CO$_3$ (2 eq). The reaction was stirred at rt for 12 h and saturated aqueous NH$_4$Cl was added. The mixture was extracted with EtOAc and the combined organic layers were washed with brine, dried over Na$_2$SO$_4$, filtered and concentrated. The residue was purified by flash chromatography on silica gel eluted with 100% EtOAc and concentrated. The neutral amine was dissolved in Et$_2$O and an excess of 2M HCl in Et$_2$O was added. The mixture was stirred for 2 h and concentrated. The residue was dissolved in water and freeze dried to give the titled compound. $^1$H NMR (acetone-d6, 500 M Hz): δ 7.76 (d, 2H), 7.44 (d, 2H), 7.21–7.13 (m, 5H), 5.41 (s, 2H), 4.78–4.74 (m, 2H), 4.53 (t, 2H), 4.08 (t, 2H), 3.44–3.40 (m, 2H), 3.04 (s, 3H), 3.04–3.0 (m, 4H), 1.76–1.71 (m, 2H), 1.65–1.60 (m, 2H), 1.45–1.40 (m, 2H), 1.22 (t, 6H).

Example 15 methyl (2Z)-3-[4-(methylsulfonyl)phenyl]-4-[({3-[(nitrooxy)methyl]phenoxy}carbonyl)oxy]-2-phenyl-but-2-enoate

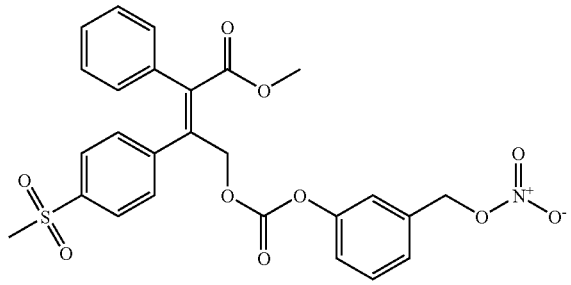

Step 1: 3-({[tert-butyl(dimethyl)silyl]oxy}methyl)phenol

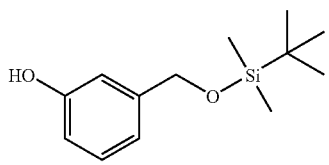

To a solution of 79 g of 3-(hydroxymethyl)phenol in 300 mL of DMF cooled at 0° C. was added 50 g of imidazole followed by 101 g of tert-butyl(chloro)dimethylsilane. The reaction was warmed to rt and stirred overnight. The reaction was quenched with aqueous $NH_4Cl$, extracted with EtOAc and washed with brine, dried over sodium sulfate, evaporated, and purified by flash chromatography (10–30% EtOAc/hexane) to afford 140 g of the title compound as a yellow oil.

Step 2: 3-({[tert-butyl(dimethyl)silyl]oxy}methyl)phenyl (2Z)-4-hydroxy-2-[4-(methylsulfonyl)phenyl]-3-phenylbut-2-enyl carbonate

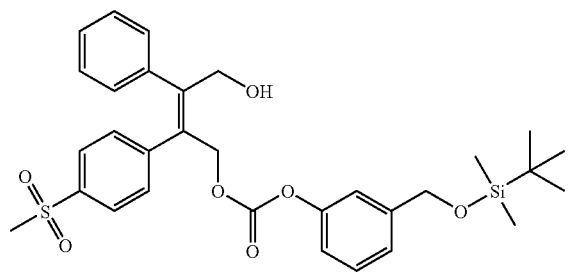

To a solution of 3.06 g of 3-({[tert-butyl(dimethyl)silyl]oxy}methyl)phenol and 1.50 g of triphosgene in 20 mL of $CH_2Cl_2$ cooled at –78° C. was added 1.2 mL of pyridine. The reaction mixture was warmed to rt. After 15–30 min, the white suspension was transferred to a solution containing 5.95 g of (2Z)-2-[4-(methylsulfonyl)phenyl]-3-phenylbut-2-ene-1,4-diol and 1.5 mL of pyridine in 20 mL of $CH_2Cl_2$ at rt. The reaction was stirred at rt for 15 min. The reaction was quenched with aqueous 1N HCl, extracted with EtOAc and washed with brine, dried over sodium sulfate, evaporated, and purified by flash chromatography (50–70% EtOAc/hexane) to afford 1.26 g of the title compound as a yellow oil.

Step 3: methyl (2Z)-4-({[3-({[tert-butyl(dimethyl)silyl]oxy}methyl)phenoxy]carbonyl}oxy)-3-[4-(methylsulfonyl)phenyl]-2-phenylbut-2-enoate

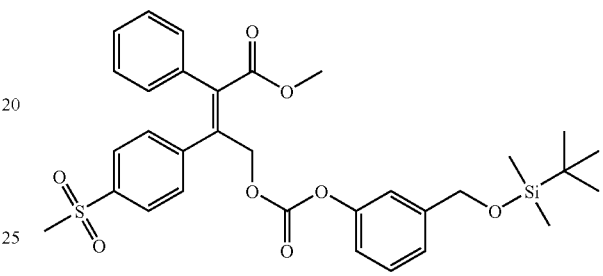

To a solution of 1.26 g of 3-({[tert-butyl(dimethyl)silyl]oxy}methyl)phenyl (2Z)-4-hydroxy-2-[4-(methylsulfonyl)phenyl]-3-phenylbut-2-enyl carbonate in 35 mL of $CH_2Cl_2$ cooled at –78° C. was added 1.05 g of Dess-Martin reagent. After 1 h of stirring at rt, the reaction was quenched with aqueous $NaHCO_3$, extracted with EtOAc, washed with aqueous $NaHCO_3$ and brine, dried over sodium sulfate, filtered through a pad of silica gel by eluting with EtOAc and evaporated. The crude material obtained was dissolved in a solvents mixture of 175 mL of t-BuOH and 75 mL of $H_2O$, and treated with 6.07 g of $NaH_2PO_4$ mono hydrated and 6.07 g of $NaClO_2$ for 30 min in the presence of 30 mL of 2-methyl-2-butene. The organic solvents were removed under vacuum. The crude material was diluted with EtOAc, washed with aqueous 1N HCl and brine, dried over $Na_2SO_4$, and evaporated. The crude acid obtained was diluted with THF and esterified with diazomethane (excess). The reaction mixture was concentrated and the residue was purified by flash chromatography (10–50% EtOAc/hexane) to afford 1.02 g of the title compound as a colorless oil.

Step 4: methyl (2Z)-4-({[3-(hydroxymethyl)phenoxy]carbonyl}oxy-3-[4-(methylsulfonyl)phenyl]-2-phenylbut-2-enoate

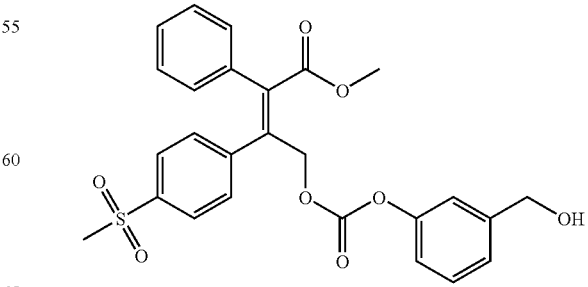

A solution of 1.02 g of methyl (2Z)-4-({[3-({[tert-butyl(dimethyl)silyl]oxy}methyl)phenoxy]carbonyl}oxy)-3-[4-

(methylsulfonyl)phenyl]-2-phenylbut-2-enoate in 20 mL of acetonitrile was treated with 1 mL of Py•HF at rt for 1 h. The reaction was quenched with aqueous $CuSO_4$, extracted twice with EtOAc and washed with aqueous $CuSO_4$ and brine, dried over sodium sulfate, evaporated, and purified by flash chromatography (50–70% EtOAc/hexane) to afford 798 mg of the title compound as a colorless oil.

Step 5: methyl (2Z)-4-({[3-(bromomethyl)phenoxy] carbonyl}oxy)-3-[4-(methylsulfonyl)phenyl]-2-phenylbut-2-enoate

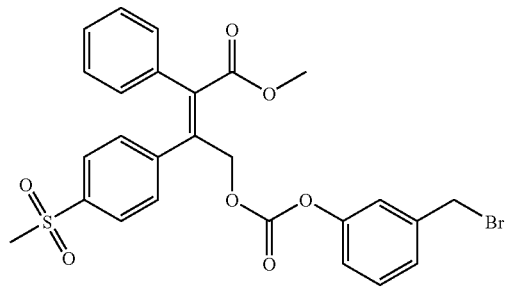

To a solution of 470 mg of $Ph_3P$ in 15 mL of $CH_2Cl_2$ cooled at 0° C. was added 1.75 mL of a 1.0M $Br_2$ solution in $CH_2Cl_2$. After 10 min, 340 µL of Hunig's base was added followed by 798 mg of methyl (2Z)-4-({[3-(hydroxymethyl) phenoxy]carbonyl}oxy)-3-[4-(methylsulfonyl)phenyl]-2-phenylbut-2-enoate dissolved in 20 mL of $CH_2Cl_2$. After 15 min at 0° C., the reaction mixture was warmed to rt for 1 h. The reaction was quenched with $H_2O$, extracted twice with EtOAc and washed with brine, dried over sodium sulfate, evaporated, and purified by flash chromatography (10–50% EtOAc/hexane) to afford 786 mg of the title compound as a colorless oil.

Step 6: methyl (2Z)-3-[4-(methylsulfonyl)phenyl]-4-[({3-[(nitrooxy)methyl]phenoxy}carbonyl)oxy]-2-phenylbut-2-enoate

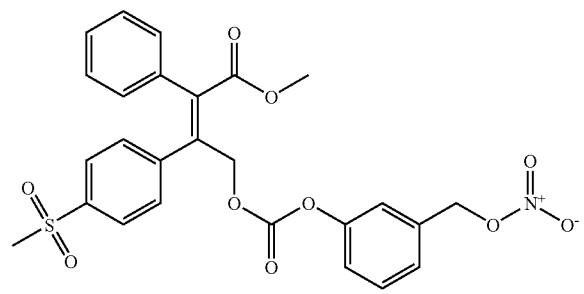

A solution of 786 mg of methyl (2Z)-4-({[3-(bromomethyl)phenoxy]carbonyl}oxy)-3-[4-(methylsulfonyl)phenyl]-2-phenylbut-2-enoate and 485 mg of $AgNO_3$ in 25 mL of acetonitrile was heated to 45° C. for 2 h. The reaction was cooled down and filtered through a pad of silica gel by eluting with EtOAc and the solvents were evaporated. The residue was purified by flash chromatography over silica gel (10–40% EtOAc/hexane) to afford 537 mg of the title compound as a waxy solid. $^1H$ NMR (acetone-d6, 500 MHz): δ 7.80 (m, 2H), 7.50–7.45 (m, 3H), 7.40 (d, 1H), 7.24 (t, 1 H), 7.19–7.14 (m, 4H), 7.11–7.09 (m, 2H), 5.58 (s, 2H), 5.44 (s, 2H), 3.81 (s, 3H), 3.06 (s, 3H).

What is claimed is:
1. A compound of Formula I

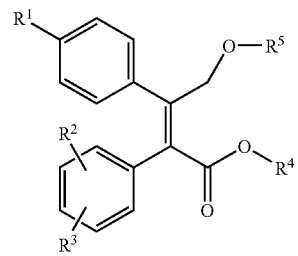

or a pharmaceutically acceptable salt thereof, wherein
$R^1$ is selected from the group consisting of:
  (a) $S(O)_2CH_3$,
  (b) $S(O)_2NH_2$,
  (c) $S(O)_2NHC(O)CF_3$,
  (d) $S(O)(NH)CH_3$,
  (e) $S(O)(NH)NH_2$,
  (f) $S(O)(NH)NHC(O)CF_3$,
  (g) $P(O)(CH_3)OH$, and
  (h) $P(O)(CH_3)NH_2$;
$R^2$ and $R^3$ each are independently selected from the group consisting of:
  (a) hydrogen,
  (b) halo,
  (c) $C_{1-6}$alkoxy,
  (d) $C_{1-6}$alkylthio,
  (e) CN,
  (f) $CF_3$,
  (g) $C_{1-6}$alkyl, and
  (h) $N_3$;
$R^4$ is selected from the group consisting of
  (a) hydrogen,
  (b) $C_{1-6}$alkyl, optionally substituted with 1–3 substituents independently selected from the group consisting of:
    (i) halo,
    (ii) phenyl, naphthyl or $HET^1$, each of said phenyl, naphthyl or $HET^1$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$,
    (iii) $N(R^i)R^{ii}$, wherein $R^i$ and $R^{ii}$ are each independently selected from the group consisting of hydrogen and $C_{1-4}$alkyl,
    (iv) $-CO_2R^{iii}$, wherein $R^{iii}$ is hydrogen or $C_{1-4}$alkyl,
  (c) phenyl, naphthyl or $HET^2$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
$R^5$ is selected from the group consisting of:

(a) $-NO_s$,
  (b) $-C(O)-E-C_{1-10}alkyl-W-NO_s$,

-continued (c) 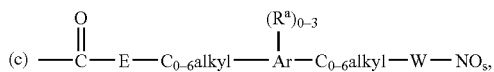

wherein:
each s is independently 1 or 2,
E is a bond, oxygen, sulfur or —C(O)—O—,
each W is independently selected from the group consisting of:

(1) oxygen, (2) sulfur, (3) 

(4) 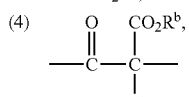

Ar is selected from the group consisting of: phenyl, naphthyl and HET$^3$,
each R$^a$ is independently selected from the group consisting of:
  (1) halo,
  (2) $C_{1-6}$alkyl,
  (3) $C_{1-6}$alkoxy,
  (4) $C_{1-6}$alkylthio,
  (5) OH,
  (6) CN,
  (7) $CF_3$,
  (8) $CO_2R^7$, and
  (9) $C_{0-6}$alkyl-W—NO$_s$;
each Rb is independently selected from the group consisting of:
  (1) $C_{1-6}$alkyl, optionally substituted with 1–3 halo groups or optionally substituted with phenyl, naphthyl or HET$^4$, each of said phenyl, naphthyl or HET$^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and
  (2) phenyl, naphthyl or HET$^5$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;
R$^6$, R$^7$ and R$^8$ are each independently selected from the group consisting of
  (a) hydrogen,
  (b) $C_{1-6}$alkyl; and
HET$^1$, HET$^2$, HET$^3$, HET$^4$ and HET$^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

2. A compound according to claim 1 of Formula I

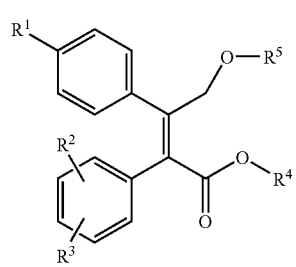

I or a pharmaceutically acceptable salt thereof, wherein
R$^1$ is selected from the group consisting of:
  (a) $S(O)_2CH_3$,
  (b) $S(O)_2NH_2$,
  (c) $S(O)_2NHC(O)CF_3$,
  (d) $S(O)(NH)CH_3$,
  (e) $S(O)(NH)NH_2$,
  (f) $S(O)(NH)NHC(O)CF_3$,
  (g) $P(O)(CH_3)OH$, and
  (h) $P(O)(CH_3)NH_2$;
R$^2$ and R$^3$ each are independently selected from the group consisting of:
  (a) hydrogen,
  (b) halo,
  (c) $C_{1-6}$alkoxy,
  (d) $C_{1-6}$alkylthio,
  (e) CN,
  (f) $CF_3$,
  (g) $C_{1-6}$alkyl, and
  (h) $N_3$;
R$^4$ is selected from the group consisting of
  (a) hydrogen,
  (b) $C_{1-6}$alkyl, optionally substituted with 1–3 halo groups or optionally substituted with phenyl, naphthyl or HET$^1$, each of said phenyl, naphthyl or HET$^1$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
  (c) phenyl, naphthyl or HET$^2$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;

$R^5$ is selected from the group consisting of:

(a) —$NO_s$, (b) —$C(O)$—E—$C_{1-10}$alkyl—W—$NO_s$, (c) 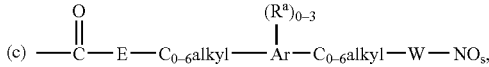

wherein:
each s is independently 1 or 2,
E is a bond, oxygen, sulfur or —C(O)—O—,
each W is independently selected from the group consisting of:

(1) oxygen,
(2) sulfur,
(3) 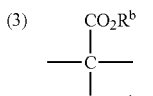
(4) 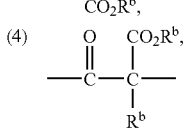

Ar is selected from the group consisting of: phenyl, naphthyl and $HET^3$,
each $R^a$ is independently selected from the group consisting of:
  (1) halo,
  (2) $C_{1-6}$alkyl,
  (3) $C_{1-6}$alkoxy,
  (4) $C_{1-6}$alkylthio,
  (5) OH,
  (6) CN,
  (7) $CF_3$,
  (8) $CO_2R^7$, and
  (9) $C_{0-6}$alkyl-W—$NO_s$;
each $R^b$ is independently selected from the group consisting of:
  (1) $C_{1-6}$alkyl, optionally substituted with 1–3 halo groups or optionally substituted with phenyl, naphthyl or $HET^4$, each of said phenyl, naphthyl or $HET^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and
  (2) phenyl, naphthyl or $HET^5$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;
$R^6$, $R^7$ and $R^8$ are each independently selected from the group consisting of
  (a) hydrogen,
  (b) $C_{1-6}$alkyl; and
$HET^1$, $HET^2$, $HET^3$, $HET^4$ and $HET^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

3. The compound according to claim 2 wherein
$R^1$ is $S(O)_2CH_3$, and
$R^2$ and $R^3$ are both hydrogen.

4. The compound according to claim 3 wherein:
$R^4$ is $C_{1-6}$alkyl, optionally substituted with 1–3 halo groups or optionally substituted with phenyl, naphthyl or $HET^1$, each of said phenyl, naphthyl or $HET^1$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
$R^6$ is selected from the group consisting of
  (a) hydrogen,
  (b) $C_{1-6}$alkyl; and
$HET^1$ is selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

5. The compound according to claim 4 wherein $R^4$ is methyl, ethyl, propyl or isopropyl.

6. The compound according to claim 3 wherein:
$R^4$ is phenyl, naphthyl or $HET^2$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
$R^6$ is selected from the group consisting of
  (a) hydrogen,
  (b) $C_{1-6}$alkyl; and
$HET^2$ is selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

7. The compound according to claim 3 wherein $R^5$ is —$NO_s$, wherein s is 1 or 2.

8. The compound according to claim 3 wherein $R^5$ is —C(O)—E—$C_{1-10}$alkyl-W—$NO_s$, wherein:
s is 1 or 2,
E is a bond, oxygen, sulfur or —C(O)—O—,
W is selected from the group consisting of:

(1) oxygen, (2) sulfur, (3)
$$-\overset{\overset{\displaystyle CO_2R^b}{|}}{\underset{\underset{\displaystyle CO_2R^b}{|}}{C}}-$$

(4)
$$-\overset{\overset{\displaystyle O}{\|}}{C}-\overset{\overset{\displaystyle CO_2R^b}{|}}{\underset{\underset{\displaystyle R^b}{|}}{C}}-$$

each $R^b$ is independently selected from the group consisting of:
(1) $C_{1-6}$alkyl, optionally substituted with 1–3 halo groups or optionally substituted with phenyl, naphthyl or $HET^4$, each of said phenyl, naphthyl or $HET^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and
(2) phenyl, naphthyl or $HET^5$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;

$R^8$ is selected from the group consisting of
(a) hydrogen and
(b) $C_{1-6}$alkyl; and $HET^4$ and $HET^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

9. The compound according to claim 8 wherein:
E is a bond or oxygen;
s is 2;
W is oxygen; and
$R^4$ is hydrogen, methyl, ethyl, propyl or isopropyl.

10. The compound according to claim 3 wherein $R^5$ is $$-\overset{\overset{\displaystyle O}{\|}}{C}-E-C_{0-6}\text{alkyl}-\!\!\!\overset{(R^a)_{0-3}}{\underset{}{\bigcirc}}\!\!\!-C_{0-6}\text{alkyl}-W-NO_s,$$

wherein:
each s independently 1 or 2,
E is a bond, oxygen, sulfur or —C(O)—O—,
each W is independently selected from the group consisting of:

(1) oxygen, (2) sulfur, (3)
$$-\overset{\overset{\displaystyle CO_2R^b}{|}}{\underset{\underset{\displaystyle CO_2R^b}{|}}{C}}-$$

(4)
$$-\overset{\overset{\displaystyle O}{\|}}{C}-\overset{\overset{\displaystyle CO_2R^b}{|}}{\underset{\underset{\displaystyle R^b}{|}}{C}}-$$

each $R^a$ is independently selected from the group consisting of:
(1) halo,
(2) $C_{1-6}$alkyl,
(3) $C_{1-6}$alkoxy,
(5) OH,
(6) CN,
(7) $CF_3$,
(8) $CO_2R^7$, and
(9) $C_{0-6}$alkyl-W—$NO_s$;

each Rb is independently selected from the group consisting of:
(1) $C_{1-6}$alkyl, optionally substituted with 1–3 halo groups or optionally substituted with phenyl, naphthyl or $HET^4$, each of said phenyl, naphthyl or $HET^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and (2) phenyl, naphthyl or HET⁵, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;

$R^7$ and $R^8$ is selected from the group consisting of
(a) hydrogen and
(b) $C_{1-6}$alkyl; and HET⁴ and HET⁵ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

11. A compound according to claim 2 of Formula II

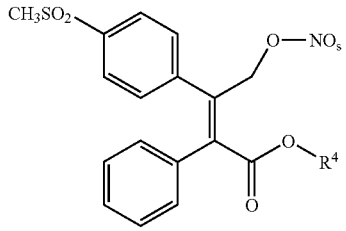

or a pharmaceutically acceptable salt thereof, wherein $R^4$ is selected from the group consisting of:
(a) $C_{1-6}$alkyl, optionally substituted with 1–3 halo groups or optionally substituted with phenyl, naphthyl or HET¹, each of said phenyl, naphthyl or HET¹ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
(b) phenyl, naphthyl or HET², each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;

$R^6$ is selected from the group consisting of
(a) hydrogen and
(b) $C_{1-6}$alkyl;
s is 1 or 2; and HET¹ and HET² are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

12. A compound according to claim 2 of Formula III

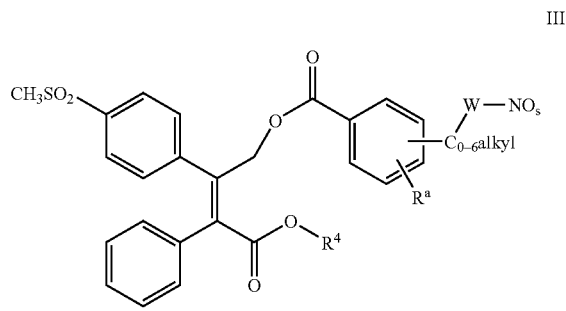

or a pharmaceutically acceptable salt thereof, wherein
$R^4$ is selected from the group consisting of:
(a) $C_{1-6}$alkyl, optionally substituted with 1–3 halo groups or optionally substituted with phenyl, naphthyl or HET¹, each of said phenyl, naphthyl or HET¹ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
(b) phenyl, naphthyl or HET², each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;

$R^6$ is selected from the group consisting of
(a) hydrogen,
(b) $C_{1-6}$alkyl;

$R^a$ is hydrogen or $C_{0-6}$alkyl-W—$NO_s$;
each s is independently 1 or 2,
each W is independently selected from the group consisting of:

(1) oxygen, (2) sulfur, (3) 
$$-\underset{\underset{CO_2R^b}{|}}{\overset{\overset{CO_2R^b}{|}}{C}}-$$

-continued (4) 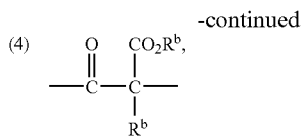

each Rb is independently selected from the group consisting of:
(1) $C_{1-6}$alkyl, optionally substituted with 1–3 halo groups or optionally substituted with phenyl, naphthyl or $HET^4$, each of said phenyl, naphthyl or $HET^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and
(2) phenyl, naphthyl or $HET^5$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;

$R^8$ is selected from the group consisting of
(a) hydrogen,
(b) $C_{1-6}$alkyl; and $HET^1$, $HET^2$, $HET^4$ and $HET^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

13. A compound according to claim 2 of Formula IV

IV

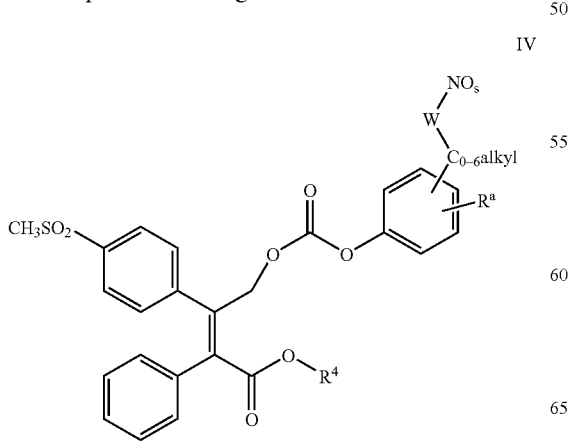

or a pharmaceutically acceptable salt thereof, wherein
$R^4$ is selected from the group consisting of:
(a) $C_{1-6}$alkyl, optionally substituted with 1–3 halo groups or optionally substituted with phenyl, naphthyl or $HET^1$, each of said phenyl, naphthyl or $HET^1$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
(b) phenyl, naphthyl or $HET^2$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;

$R^6$ is selected from the group consisting of
(a) hydrogen,
(b) $C_{1-6}$alkyl;

$R^a$ is hydrogen or $C_{0-6}$alkyl-W-$NO_s$.

each s is independently 1 or 2;

each W is independently selected from the group consisting of:
(1) oxygen,
(2) sulfur,
(3) 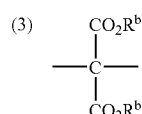
(4) 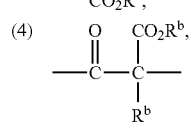

each Rb is independently selected from the group consisting of:
(1) $C_{1-6}$alkyl, optionally substituted with 1–3 halo groups or optionally substituted with phenyl, naphthyl or $HET^4$, each of said phenyl, naphthyl or $HET^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and
(2) phenyl, naphthyl or $HET^5$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;

$R^8$ is selected from the group consisting of
(a) hydrogen,
(b) $C_{1-6}$alkyl; and $HET^1$, $HET^2$, $HET^4$ and $HET^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

14. The compound according to claim 13 of Formula IVa

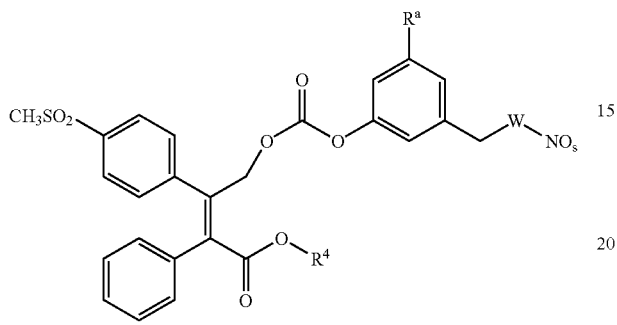

IVa or a pharmaceutically acceptable salt thereof, wherein
$R^4$ is selected from the group consisting of:
(a) $C_{1-6}$alkyl, optionally substituted with 1–3 halo groups or optionally substituted with phenyl, naphthyl or $HET^1$, each of said phenyl, naphthyl or $HET^1$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
(b) phenyl, naphthyl or $HET^2$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^6$;
$R^6$ is selected from the group consisting of
(a) hydrogen,
(b) $C_{1-6}$alkyl;
$R^a$ is hydrogen or $C_{0-6}$alkyl-W—$NO_s$;
each s is independently 1 or 2;
each W is independently selected from the group consisting of:
(1) oxygen,
(2) sulfur,
(3) 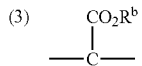
(4) 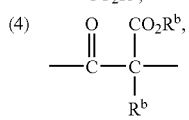

each Rb is independently selected from the group consisting of:
(1) $C_{1-6}$alkyl, optionally substituted with 1–3 halo groups or optionally substituted with phenyl, naphthyl or $HET^4$, each of said phenyl, naphthyl or $HET^4$ being optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$; and (2) phenyl, naphthyl or $HET^5$, each optionally substituted with 1–3 substituents independently selected from the group consisting of: halo, $C_{1-6}$alkyl, $C_{1-6}$alkoxy, $C_{1-6}$alkylthio, OH, CN, $CF_3$, and $CO_2R^8$;
$R^8$ is selected from the group consisting of
(a) hydrogen,
(b) $C_{1-6}$alkyl; and
$HET^1$, $HET^2$, $HET^4$ and $HET^5$ are each independently selected from the group consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

15. The compound according to claim 1 wherein: $R^4$ is $C_{1-6}$alkyl, mono-substituted with
(i) $N(R^i)R^{ii}$, wherein $R^i$ and $R^{ii}$ are each independently selected from the group consisting of hydrogen and $C_{1-4}$alkyl or
(ii) —$CO_2R^{iii}$, wherein $R^{iii}$ is hydrogen or $C_{1-4}$alkyl.

16. A compound selected from the following group:

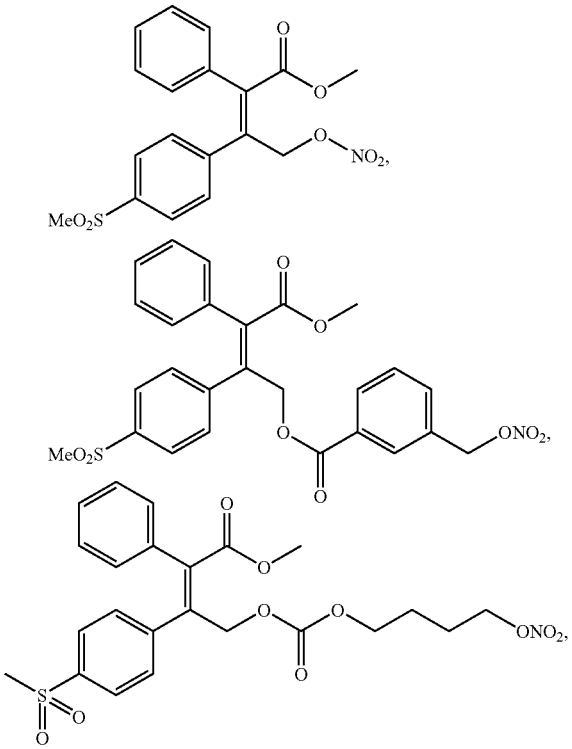

-continued
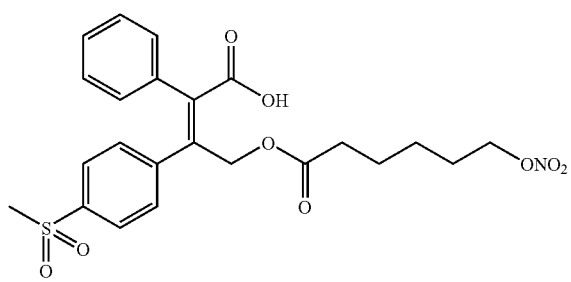
or a pharmaceutically acceptable salt thereof,
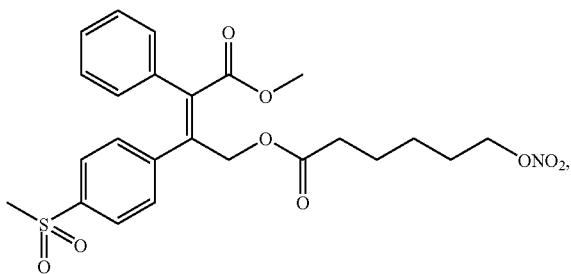
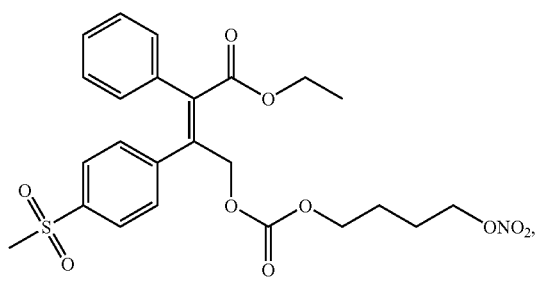
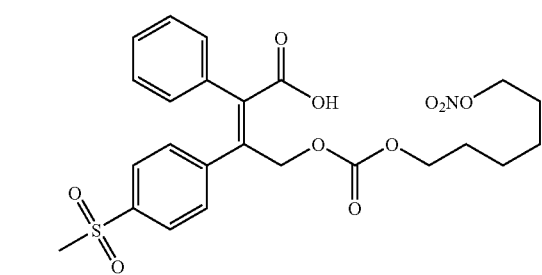
or a pharmaceutically acceptable salt thereof,
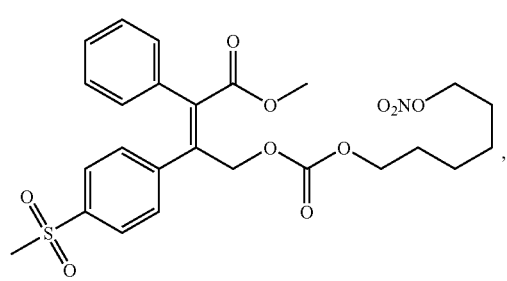
-continued
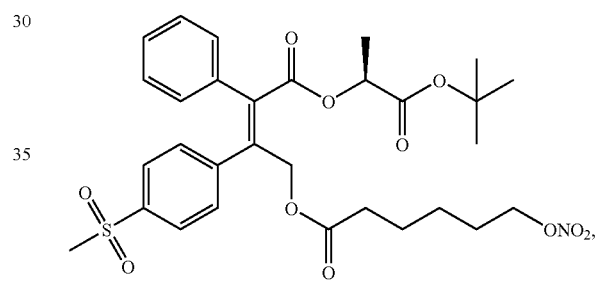
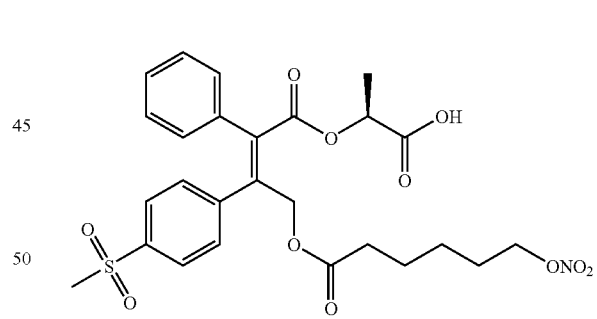
or a pharmaceutically acceptable salt thereof,
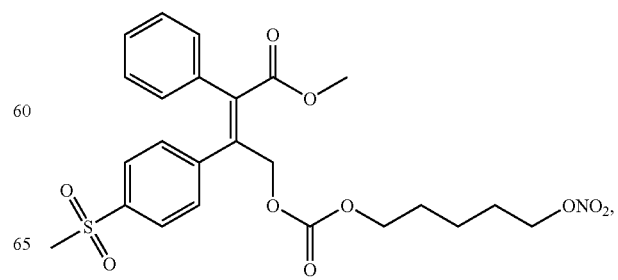
or a pharmaceutically acceptable salt thereof, -continued

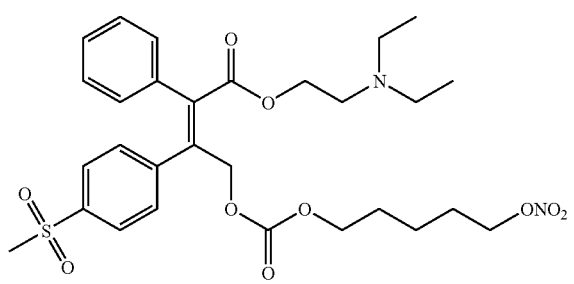

or a pharmaceutically acceptable salt thereof, and

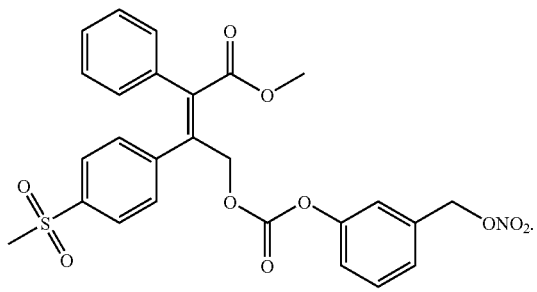

17. A method for treating a chronic cyclooxygenase-2 mediated disease or condition and reducing the risk of a thrombotic cardiovascular event in a human patient in need of such treatment and at risk of a thrombotic cardiovascular event comprising orally concomitantly or sequentially administering to said patient a compound according to claim 1 in an amount effective to treat the cyclooxygenase-2 mediated disease or condition and aspirin in an amount effective to reduce the risk of the thrombotic cardiovascular event, wherein said chronic cyclooxygenase-2 mediated disease or condition is selected from the group consisting of pain, fever and inflammation of a condition selected from the group consisting of rheumatic fever, symptoms associated with influenza, common cold, low back pain, neck pain, dysmenorrhea, headache, migraine, toothache, sprains and strains, neuralgia, synovitis, rheumatoid arthritis, osteoarthritis, gout, bursitis, burns, injuries, and pain and inflammation following surgical procedures and inhibition of the onset or progression of Alzheimer's disease.

18. A pharmaceutical composition comprising a compound of formula I according to claim 1, or a pharmaceutically acceptable salt thereof, and a pharmaceutically acceptable carrier.

* * * * *